(12) United States Patent
McDevitt et al.

(10) Patent No.: US 10,820,983 B2
(45) Date of Patent: *Nov. 3, 2020

(54) HELICOIL INTERFERENCE FIXATION SYSTEM FOR ATTACHING A GRAFT LIGAMENT TO A BONE

(71) Applicant: Smith & Nephew, Inc., Memphis, TN (US)

(72) Inventors: Dennis McDevitt, Raleigh, NC (US); Vincent Novak, Longmont, CO (US)

(73) Assignee: Healicoil, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/205,939

(22) Filed: Nov. 30, 2018

(65) Prior Publication Data
US 2019/0099255 A1   Apr. 4, 2019

Related U.S. Application Data

(60) Continuation of application No. 15/225,033, filed on Aug. 1, 2016, now abandoned, which is a
(Continued)

(51) Int. Cl.
*A61B 17/86* (2006.01)
*A61F 2/08* (2006.01)
(Continued)

(52) U.S. Cl.
CPC .......... *A61F 2/0811* (2013.01); *A61B 17/809* (2013.01); *A61B 17/861* (2013.01); *A61B 17/869* (2013.01); *A61B 17/8877* (2013.01); *A61B 17/8886* (2013.01); *A61F 2/08* (2013.01); *A61F 2/0805* (2013.01); *A61B 2017/0441* (2013.01); *A61F 2/30744* (2013.01); *A61F 2/389* (2013.01); *A61F 2002/0841* (2013.01); *A61F 2002/0858* (2013.01); *A61F 2002/0882* (2013.01); *A61F 2002/2817* (2013.01);
(Continued)

(58) Field of Classification Search
CPC ........... A61B 17/869; A61B 2017/0441; A61F 2230/0091
See application file for complete search history.

(56) References Cited

U.S. PATENT DOCUMENTS 4,961,740 A * 10/1990 Ray ..................... A61B 17/1637
606/247
5,354,299 A * 10/1994 Coleman ............ A61B 17/1615
606/916

(Continued)

*Primary Examiner* — Samuel S Hanna
(74) *Attorney, Agent, or Firm* — Burns & Levinson, LLP; Joseph M. Maraia

(57) ABSTRACT

A helicoil interference fixation system comprising:
a helicoil comprising a helical body comprising a plurality of turns separated by spaces therebetween, the helical body terminating in a proximal end and a distal end, and at least one internal strut extending between at least two turns of the helical body; and
an inserter for turning the helicoil, the inserter comprising at least one groove for receiving the at least one strut; the helicoil being mounted on the inserter such that the at least one strut of the helicoil is mounted in the at least one groove of the inserter, such that rotation of the inserter causes rotation of the helicoil.

20 Claims, 30 Drawing Sheets

Related U.S. Application Data continuation of application No. 14/550,248, filed on Nov. 21, 2014, now Pat. No. 9,579,189, which is a division of application No. 12/392,804, filed on Feb. 25, 2009, now Pat. No. 8,894,661, which is a continuation-in-part of application No. 11/893,440, filed on Aug. 16, 2007, now abandoned.

(60) Provisional application No. 60/838,119, filed on Aug. 16, 2006, provisional application No. 61/200,285, filed on Nov. 26, 2008.

(51) Int. Cl.
*A61B 17/80* (2006.01)
*A61B 17/88* (2006.01)
*A61B 17/04* (2006.01)
*A61F 2/30* (2006.01)
*A61F 2/38* (2006.01)
*A61F 2/28* (2006.01)

(52) U.S. Cl.
CPC ........... *A61F 2002/2835* (2013.01); *A61F 2002/30062* (2013.01); *A61F 2002/3085* (2013.01); *A61F 2002/30266* (2013.01); *A61F 2002/30299* (2013.01); *A61F 2002/30329* (2013.01); *A61F 2002/30593* (2013.01); *A61F 2002/30736* (2013.01); *A61F 2002/30772* (2013.01); *A61F 2210/0004* (2013.01); *A61F 2220/0025* (2013.01); *A61F 2230/0082* (2013.01); *A61F 2230/0091* (2013.01); *A61F 2230/0093* (2013.01); *A61F 2310/00017* (2013.01)

(56) References Cited

U.S. PATENT DOCUMENTS

| | | | | |
|---|---|---|---|---|
| 5,695,497 | A | * | 12/1997 | Stahelin .............. F16B 23/0007 606/104 |
| 2003/0125749 | A1 | * | 7/2003 | Yuan .................. A61B 17/8875 606/104 |
| 2006/0247642 | A1 | * | 11/2006 | Stone ................. A61B 17/8605 623/13.14 |

* cited by examiner

HELICOIL INTERFERENCE FIXATION SYSTEM FOR ATTACHING A GRAFT LIGAMENT TO A BONE

REFERENCE TO PENDING PRIOR PATENT APPLICATIONS

This application is a continuation of co-pending U.S. application Ser. No. 15/225,033, filed Aug. 1, 2016, entitled HELICOIL INTERFERENCE FIXATION SYSTEM FOR ATTACHING A GRAFT LIGAMENT TO A BONE, which in turn is a continuation of U.S. application Ser. No. 14/550,248, filed Nov. 21, 2014, now U.S. Pat. No. 9,579,189, which in turn is a divisional of U.S. application Ser. No. 12/392,804, filed Feb. 25, 2009, now U.S. Pat. No. 8,894,661, which in turn is a continuation-in-part of U.S. application Ser. No. 11/893,440, filed Aug. 16, 2007, which in turn claims priority to and benefit of U.S. Provisional Application No. 60/838,119, filed Aug. 16, 2006. U.S. application Ser. No. 12/392,804 also claims priority to and benefit of U.S. Provisional Application No. 61/200,285, filed Nov. 26, 2008. Each of the above-referenced applications are incorporated herein by reference in their entirety for all purposes.

FIELD OF THE INVENTION

This invention relates to medical apparatus and procedures in general, and more particularly to medical apparatus and procedures for reconstructing a ligament.

BACKGROUND OF THE INVENTION

Ligaments are tough bands of tissue which serve to connect the articular extremities of bones, and/or to support and/or retain organs in place within the body. Ligaments are typically made up of coarse bundles of dense fibrous tissue which are disposed in a parallel or closely interlaced manner, with the fibrous tissue being pliant and flexible but not significantly extensible.

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. The ACL and PCL serve, together with other ligaments and soft tissue, to provide both static and dynamic stability to the knee. Often, the anterior cruciate ligament (i.e., the ACL) is ruptured or torn as the result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere within the patient's body, e.g., a patella tendon with or without bone blocks attached, a semitendinosus tendon and/or a gracilis tendon. In other circumstances, the graft ligament may be harvested from a cadaver. In still other circumstances, the graft ligament may be a synthetic device. For the purposes of the present invention, all of the foregoing may be collectively referred to herein as a "graft ligament".

As noted above, various approaches are well known in the art for anchoring the two ends of the graft ligament in the femoral and tibial bone tunnels.

In one well-known procedure, which may be applied to femoral fixation, tibial fixation, or both, the end of the graft ligament is placed in the bone tunnel, and then the graft ligament is fixed in place using a headless orthopedic screw, generally known in the art as an "interference" screw. More particularly, with this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft, ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel. However, the interference screw itself generally takes up a substantial amount of space within the bone tunnel, which can limit the surface area contact established between the graft ligament and the side wall of the bone tunnel. This in turn limits the region of bone-to-ligament in-growth, and hence can affect the strength of the joinder. By way of example but not limitation, it has been estimated that the typical interference screw obstructs about 50% of the potential bone-to-ligament integration region.

For this reason, substantial efforts have been made to provide interference screws fabricated from absorbable materials, so that the interference screw can eventually disappear over time and bone-to-ligament in-growth can take place about the entire perimeter of the bone tunnel. To this end, various absorbable interference screws have been developed which are made from biocompatible, bioabsorbable polymers, e.g., polylactic acid (PLA), polyglycolic acid (PGA), etc. These polymers generally provide the substantial mechanical strength needed to advance the interference screw into position, and to thereafter hold the graft ligament in position while bone-to-ligament in-growth occurs, without remaining in position on a permanent, basis.

In general, interference screws made from such biocompatible, bioabsorbable polymers have proven clinically successful. However, these absorbable interference screws still suffer from several disadvantages. First, clinical evidence suggests that the quality of the bone-to-ligament in-growth is somewhat different than natural bone-to ligament in-growth, in the sense that the aforementioned bioabsorbable polymers tend to be replaced by a fibrous mass rather than a well-ordered tissue matrix. Second, clinical evidence suggests that absorption generally takes a substantial period of time, e.g., on the order of three years or so. Thus, during this absorption time, the bone-to-ligament in-growth is still significantly limited by the presence of the interference screw. Third, clinical evidence suggests that, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

Thus, there is a need for a new and improved interference fixation system which (i) has the strength needed to hold the graft ligament in position while bone-to-ligament in-growth occurs, and (ii) promotes superior bone-to-ligament in-growth.

SUMMARY OF THE INVENTION

These and other objects are addressed by the provision and use of a novel helicoil interference fixation system for attaching a graft ligament to a bone.

In one preferred form of the invention, there is provided at novel helicoil interference fixation system comprising:

a helicoil comprising a helical body comprising a plurality of turns separated by spaces therebetween, the helical body terminating in a proximal end and a distal end, and at least one internal strut extending between at least two turns of the helical body; and an inserter for turning the helicoil, the inserter comprising at least one groove for receiving the at least one strut;

the helicoil being mounted on the inserter such that the at least one strut of the helicoil is mounted in the at least one groove of the inserter, such that rotation of the inserter causes rotation of the helicoil.

In another preferred form of the invention, there is provided a novel method for attaching a graft ligament to a bone, the method comprising:

providing a helicoil interference fixation system comprising:

a helicoil comprising a helical body comprising a plurality of turns separated by spaces therebetween, the helical body terminating in a proximal end and a distal end, and at least one internal strut extending between at least two turns of the helical body; and an inserter for turning the helicoil, the inserter comprising at least one groove for receiving the at least one strut;

the helicoil being mounted on the inserter such that the at least one strut of the helicoil is mounted in the at least one groove of the inserter, such that rotation of the inserter causes rotation of the helicoil;

forming a bone tunnel in the bone, and providing a graft ligament;

inserting the graft ligament into the bone tunnel; and using the inserter to turn the helicoil into the bone tunnel so as to secure the graft ligament to the bone using an interference fit.

In another preferred form of the invention, there is provided a novel helicoil comprising a helical body comprising a plurality of turns separated by spaces therebetween, the helical body terminating in a proximal end and a distal end, and at least one internal strut extending between at least two turns of the helical body, wherein the at least one internal strut comprises a helical construction.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention comprises the provision and use of a novel helicoil interference fixation system for attaching a graft ligament to a bone or other tissue.

For convenience, the present invention will hereinafter be discussed in the context of its use for an ACL tibial and/or femoral fixation; however, it should be appreciated that the present invention may also be used for the fixation of other graft ligaments to the tibia and/or the femur; and/or the fixation of other graft ligaments to other bones or to other tissue such as organs.

Looking first at FIGS. 1-7, there is shown a novel helicoil interference fixation system 5 for securing a graft ligament to a bone. Helicoil interference fixation system 5 generally comprises a helicoil 10 for disposition in a bone tunnel so as to hold the graft ligament in position while bone-to-ligament in-growth occurs. Helicoil interference fixation system 5 also comprises an inserter 15 for deploying helicoil 10 in the bone tunnel.

Figure 1:
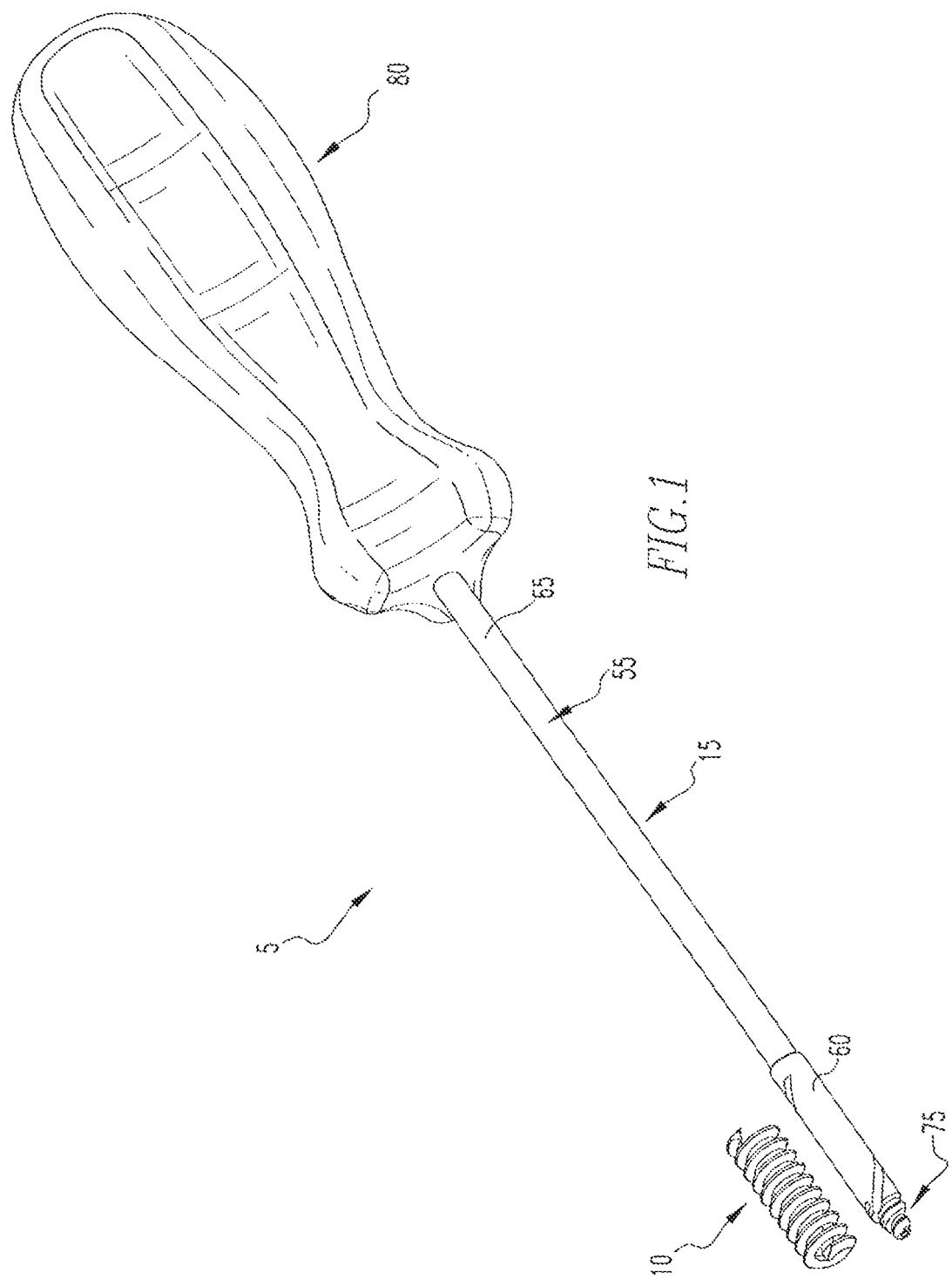
FIGS. 1-7 are schematic views showing a first helicoil interference fixation system formed in accordance with the present invention.
Figure 2:
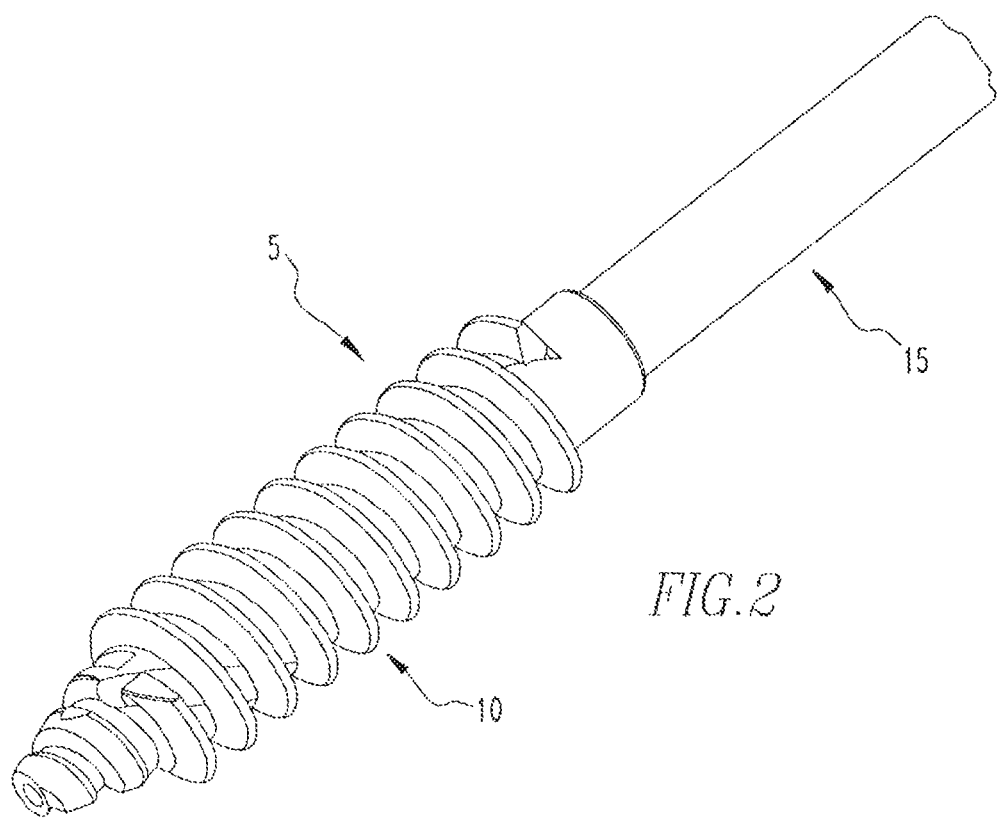
Figure 3:
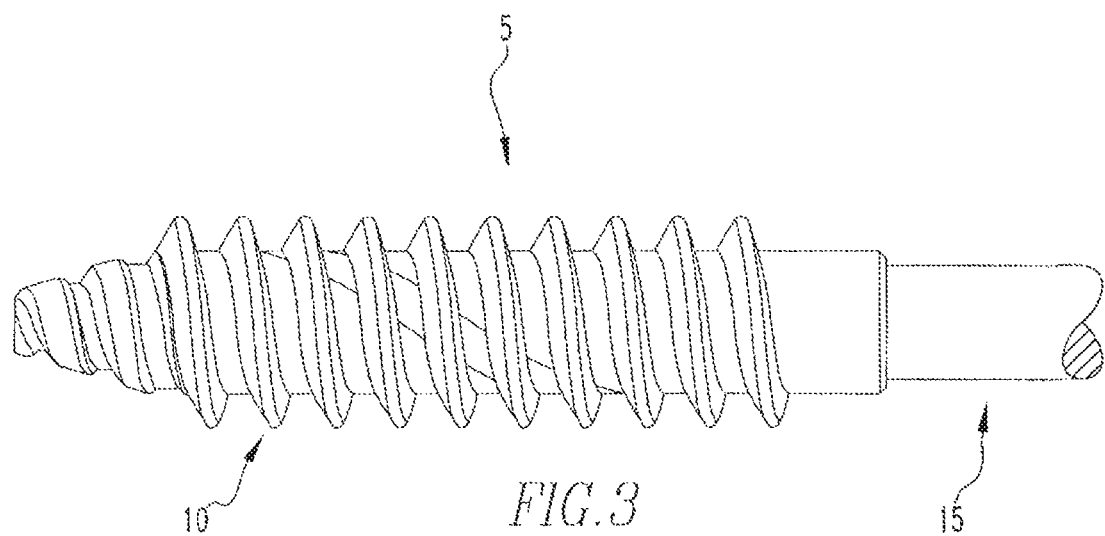
Figure 4:
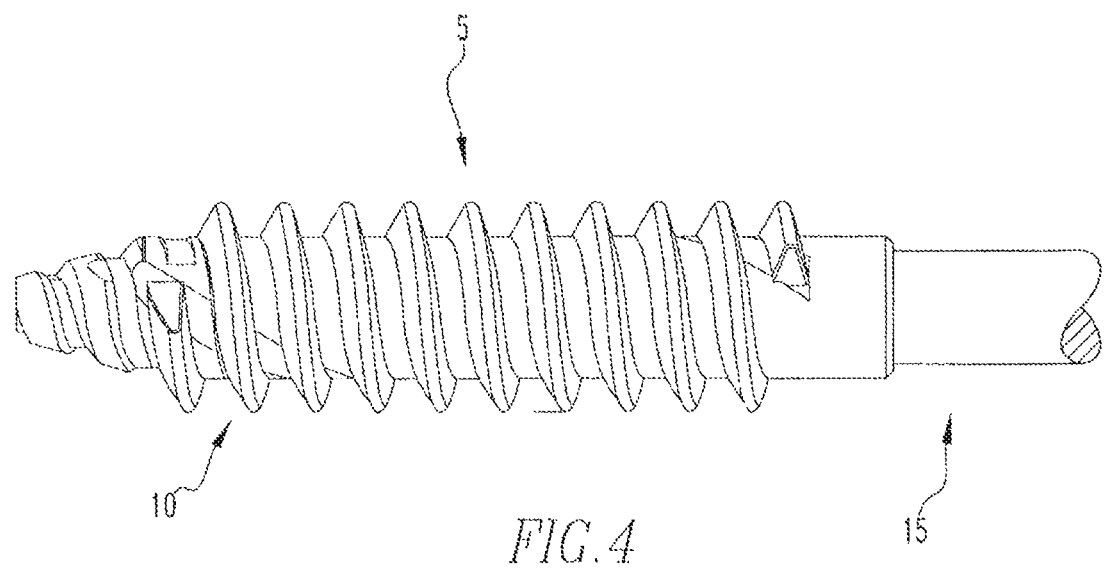
Figure 5:
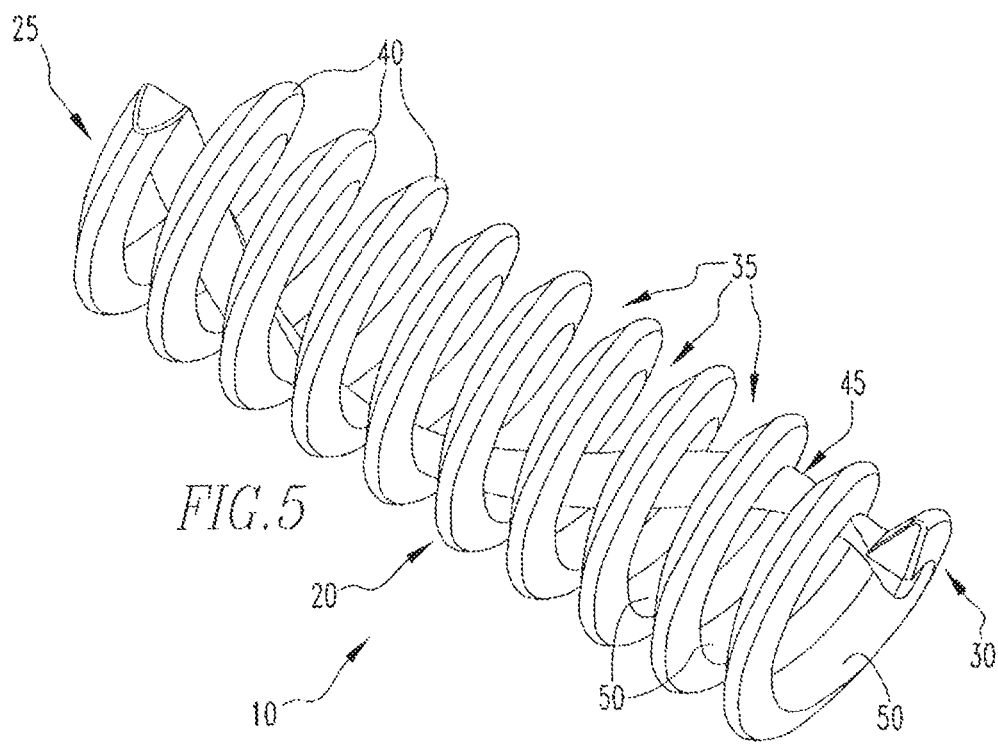
Figure 6:
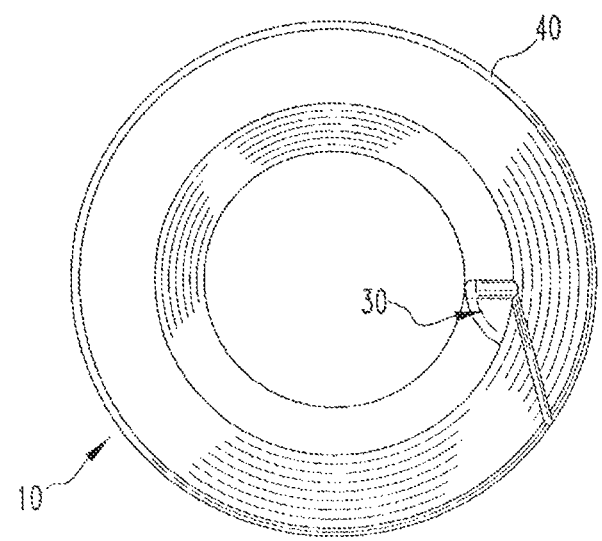
Figure 7:
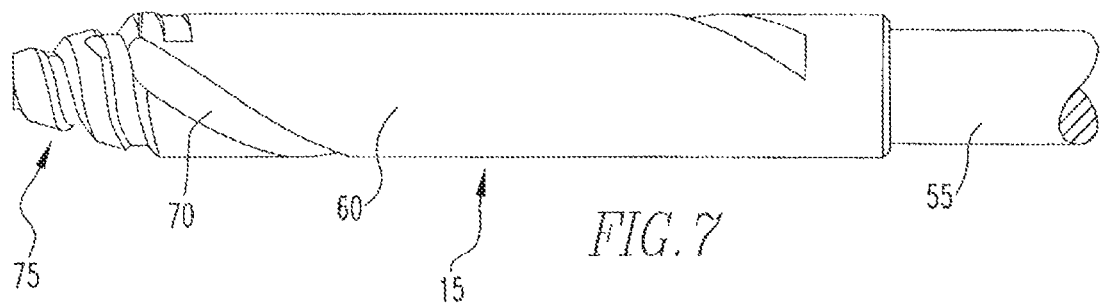
Figure 8:
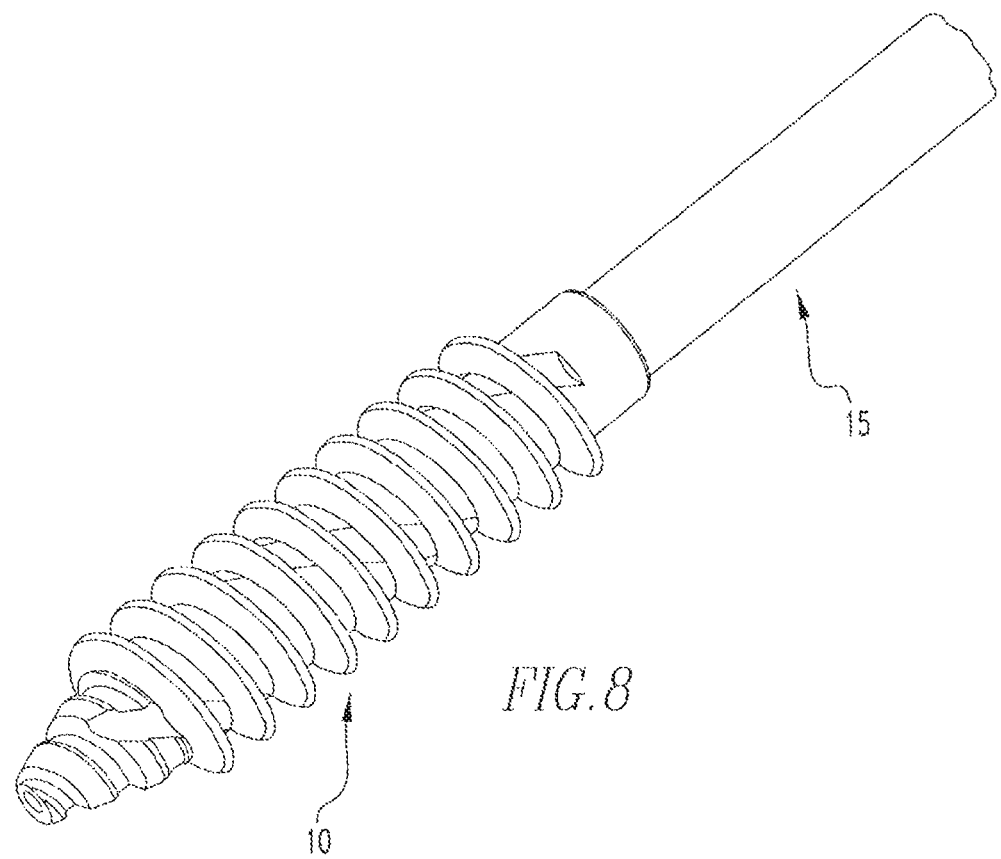
FIGS. 8-13 are schematic views showing a second helicoil interference fixation system formed in accordance with the present invention.
Figure 9:
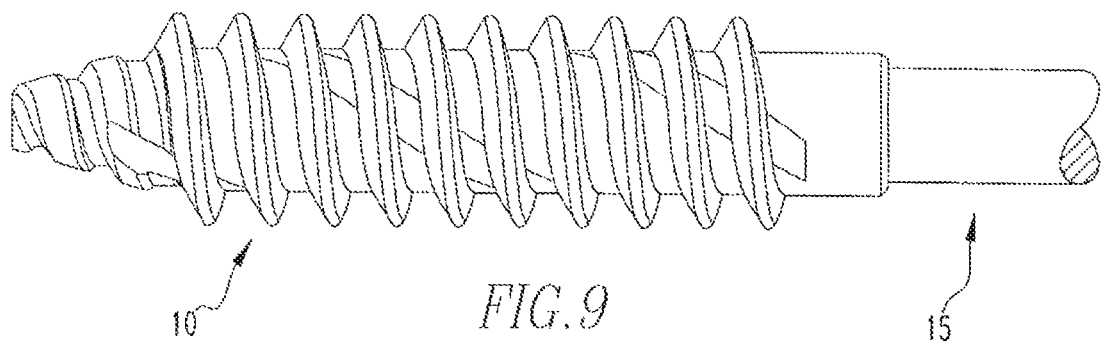
Figure 10:
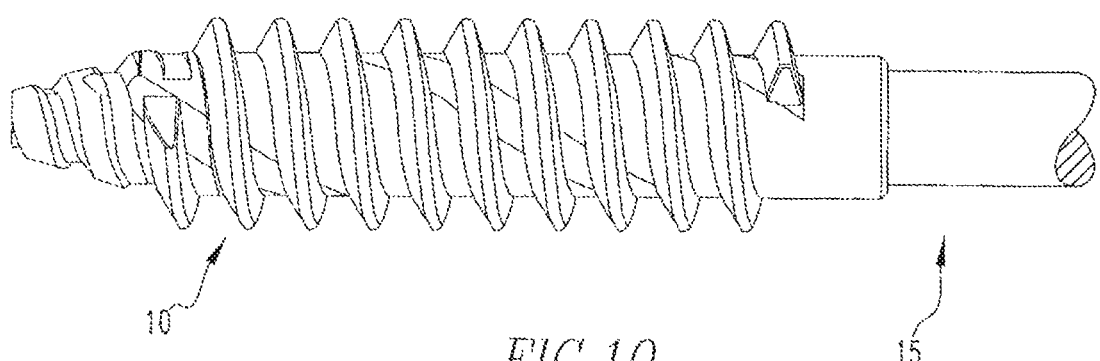

More particularly, and looking now at FIGS. 1-6, and particularly at FIG. 5, helicoil 10 generally comprises a helical body 20 terminating in a distal end 25 and a proximal end 30. Helical body 20 is constructed so that there are substantial spaces or gaps 35 between the turns 40 of the helical body. Spaces or gaps 35 facilitate bone-to-ligament in-growth, i.e., by providing large openings through the helical body. These large openings facilitate the flow of cell- and nutrient-bearing fluids through the helicoil, and permit the in-growth of tissue across the helicoil, so as to enhance bone-to-ligament in-growth.

One or more struts 45 are disposed within the interior of helical body 20, with the one or more struts 45 being secured to the interior surfaces 50 of helical body 20. The one or more struts 45 provide a means for turning helicoil 10 during deployment within the body, as will hereinafter be discussed in further detail. In addition, the one or more struts 45 can provide structural support for the turns 40 of helical body 20. The one or more struts 45 may be formed integral with helical body 20 (e.g., by a molding process), or they may be formed separately from helical body 20 and then attached to helical body 20 in a separate manufacturing process (e.g., by welding). Where the one or more struts 45 are formed integral with helical body 20, the one or more struts 45 can be used to help flow melt into position.

In one preferred form of the invention, the one or more struts 45 comprise helical structures. And in one particularly preferred form of the invention, the one or more struts 45 comprise helical structures which spiral in the opposite direction from the spiral of helical body 20, and the one or more struts 45 have a pitch which is substantially greater than the pitch of helical body 20. See FIG. 5.

Preferably, the number of struts 45, and their size, are selected so as to close off an insignificant portion of the spaces or gaps 35 between the turns 40 of helical body 20, whereby to substantially not impede the passage of fluids and tissue through the helicoil. At the same time, however, the number of struts 45, their size, and composition, are selected so as to provide an adequate means for turning helicoil 10 during deployment, and to provide any necessary support for the turns 40 of helical body 20.

In one preferred form of the present invention, one strut 45 is provided.

In another preferred form of the present invention, a plurality of struts 45 (e.g., two, three, four or more struts) are provided.

And in one preferred form of the present invention, the struts 45 collectively close off less than fifty percent (50%) of the spaces or gaps 35 between the turns 40 of helical body 20.

And in one particularly preferred form of the present invention, the struts 45 collectively close off less than twenty percent (20%) of the spaces or gaps 35 between the turns 40 of helical body 20.

Helicoil 10 is formed out of one or more biocompatible materials. These biocompatible materials may be non-absorbable (e.g., stainless steel or plastic) or absorbable (e.g., a bioabsorbable polymer). In one preferred form of the present invention, helicoil 10 preferably comprises a bioabsorbable polymer such as polylactic acid (PLA), polyglycolic acid (PGA), etc. In any case, however, helicoil 10 comprises a material which is capable of providing the strength needed to set the fixation device into position and to hold the graft ligament in position while bone-to-ligament in-growth occurs.

Inserter 15 is shown in FIGS. 1-4 and 7. Inserter 15 generally comprises a shaft 55 having a distal end 60 and a proximal end 65. One or more grooves 70 are formed on the distal end of shaft 55. Grooves 70 receive the one or more struts 45 of helicoil 10, in order that helicoil 10 may be mounted on the distal end of shaft 55 and rotated by rotation of shaft 55. A tapered seat-forming thread 75 (e.g., a tapered cutting thread, a tapered opening or dilating thread, etc.) is formed in shaft 55 distal to grooves 70. Tapered seat-forming thread 75 serves to precede helicoil 10 into the space between the graft ligament and the wall of the bone tunnel, and then to form a lead-in or opening in the graft ligament and the wall of the bone tunnel for receiving the turns 40 of helical body 20, in much the same manner as a tap that creates the thread form, as will hereinafter be discussed in further detail. A handle 80 is mounted on the proximal end of shaft 55 in order to facilitate rotation of shaft 55 by the surgeon.

It should be appreciated that tapered seat-forming thread 75 is matched to helicoil 10 so that when helicoil 10 is mounted on inserter 15, tapered seat-forming thread 75 provides the proper lead-in for helicoil 10.

Preferably, interior surfaces 50 of helical body 20 and distal end 60 of inserter 15 are tapered, expanding outwardly in the proximal direction, so that helicoil 10 and inserter 15 form a positive seat such that the interior surface of the helicoil is in direct contact with the tapered body diameter of the inserter.

Thus it will be seen that, when helicoil 10 is mounted on the distal end of shaft 55, inserter 15 may be used to advance the helicoil to a surgical site and, via rotation of handle 80, turn helicoil 10 into the gap between a graft ligament and the wall of a bone tunnel, whereby to create an interference fixation of the graft ligament in the bone tunnel. Significantly, inasmuch as inserter 15 has a tapered seat-forming thread 75 formed on its distal end in advance of helicoil 10, the tapered seat-forming thread can form a seat into the tissue in advance of helicoil 10, whereby to permit the helicoil to advance easily into the tissue and create the desired interference fixation. Accordingly, helicoil 10 does not need to have any penetrating point on its distal end in order to penetrate the tissue.

If desired, inserter 15 may be cannulated so that the inserter and helicoil 10 may be deployed over a guidewire, as will hereinafter be discussed.

FIGS. 8-13 show another helicoil interference fixation system 5, wherein helicoil 10 comprises two struts 45 and inserter 15 comprises two grooves 70. The use of two struts 45, rather than one strut 45, may be advantageous since it may distribute the load imposed during rotation over a larger surface area. This may be important where helicoil 10 is formed out of a bioabsorbable polymer.

Helicoil interference fixation system 5 may be utilized in a manner generally similar to that of a conventional interference screw system in order to attach a graft ligament to a bone.

More particularly, and looking now at FIGS. 14-25, there are shown various aspects of an ACL reconstruction effected using helicoil interference fixation system 5.

Figure 14:
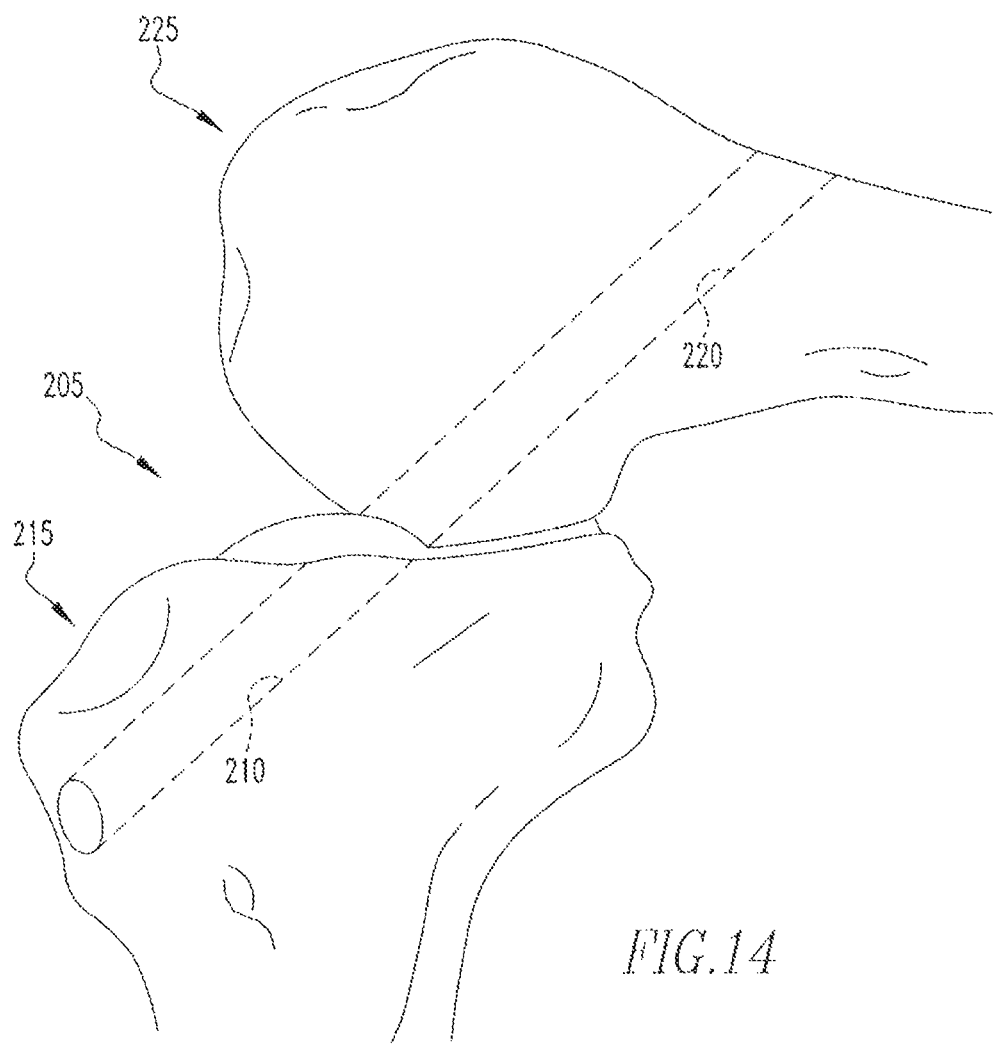
FIGS. 14-20 are schematic views showing a femoral fixation using the second helicoil interference fixation system of FIGS. 8-13.

FIG. 14 shows a typical knee joint 205, with the joint having been prepared for an ACL reconstruction, i.e., with the natural ACL having been removed, and with a tibial bone tunnel 210 having been formed in tibia 215, and with a femoral bone tunnel 220 having been formed in femur 225.

Figure 15:
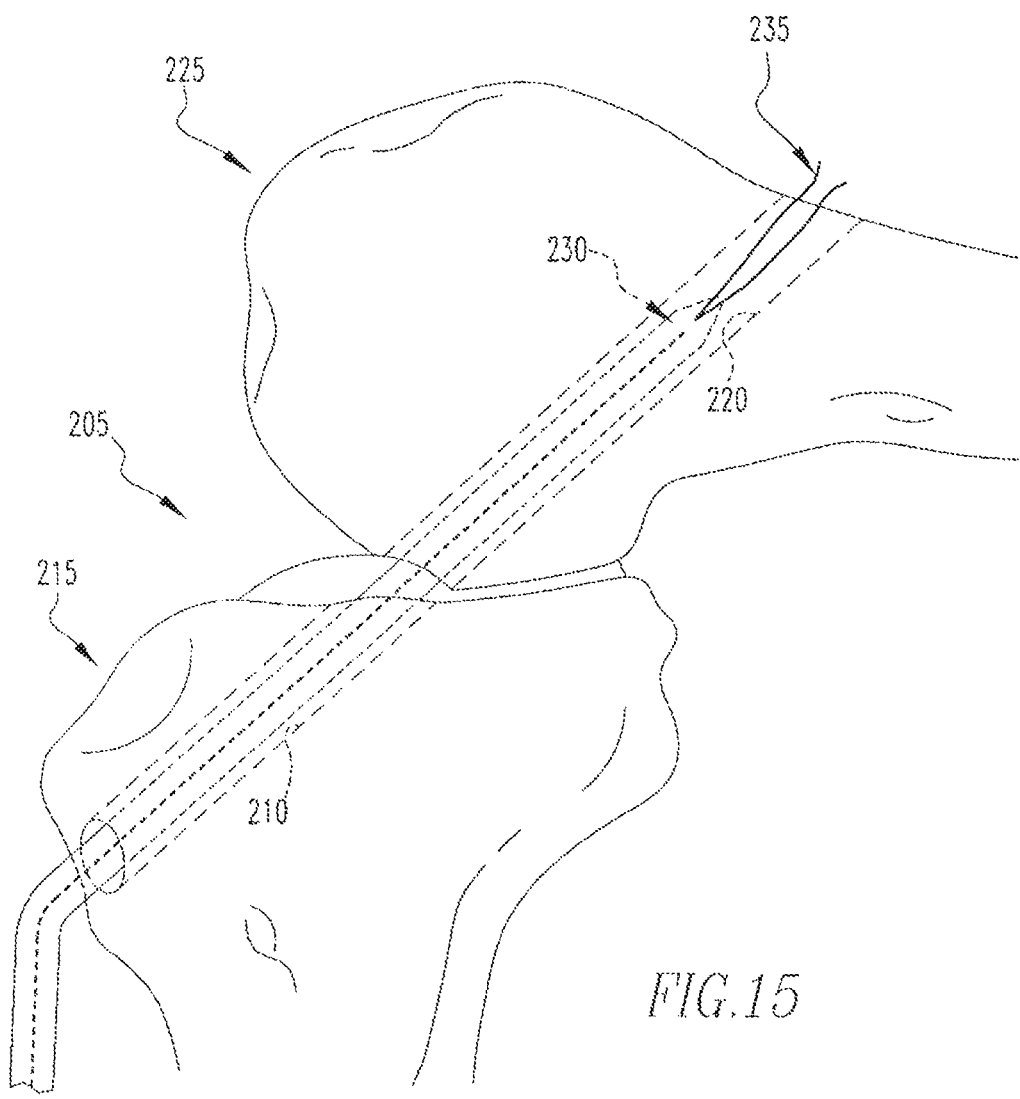

FIG. 15 is a view similar to that of FIG. 14, except that a graft ligament 230 has been positioned in femoral bone tunnel 220 and tibial bone tunnel 210 in accordance with ways well known in the art. By way of example, graft ligament 230 may be "towed" up through tibial bone tunnel 210 and into femoral bone tunnel 220 using a tow suture 235.

Figure 16:
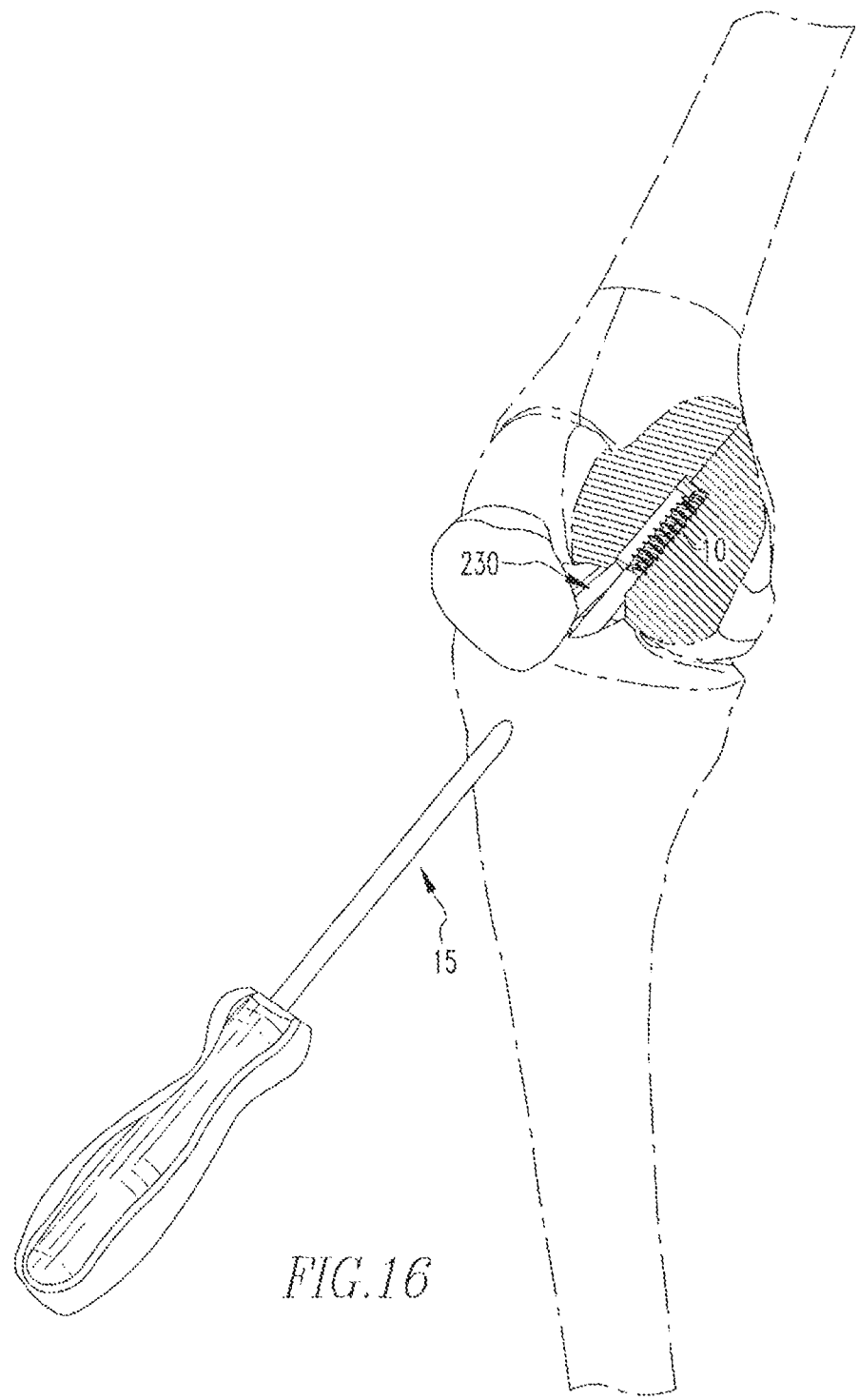
Figure 17:
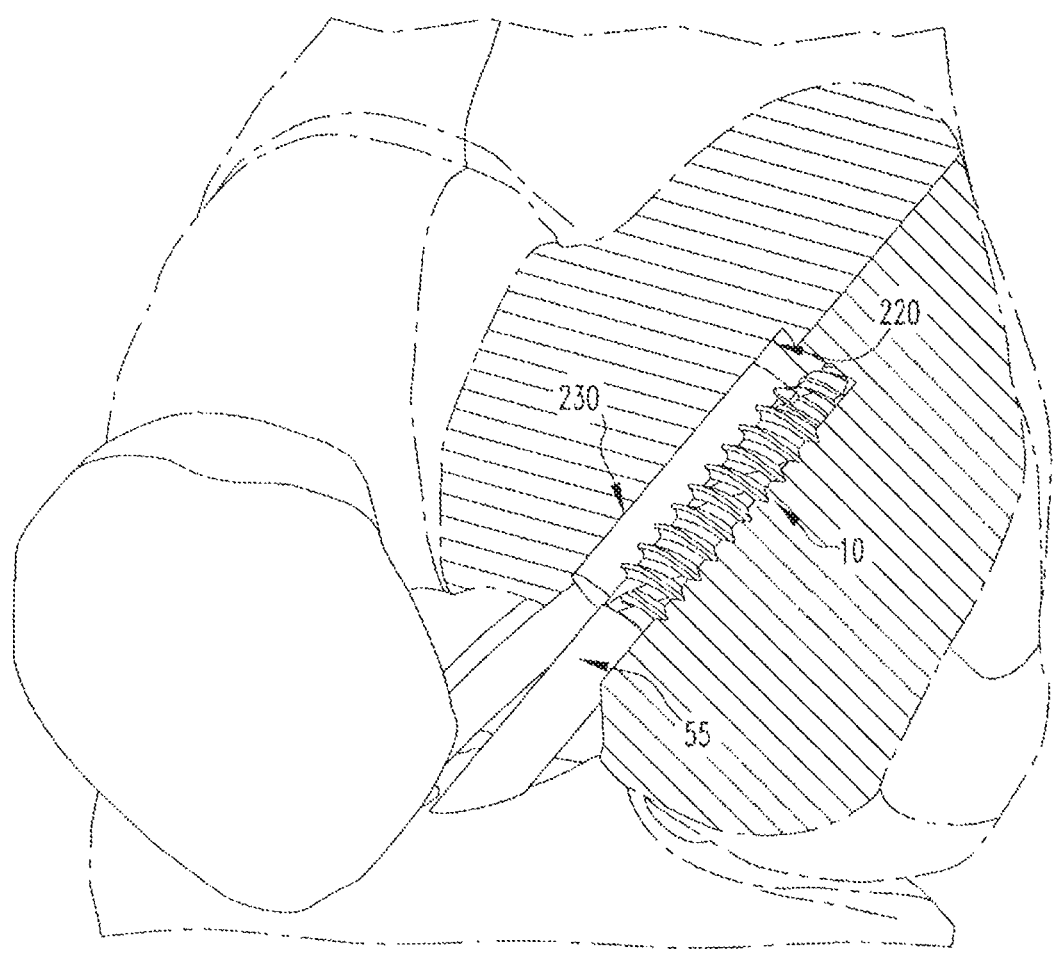

FIGS. 16 and 17 show graft ligament 230 being made fast in femoral tunnel 220 using helicoil interference fixation system 5. More particularly, in accordance with the present invention, helicoil 10 is mounted on the distal end of inserter 15 by fitting the struts 45 of helicoil 10 into the grooves 70 of the inserter. Then the inserter is used to advance helicoil 10 through tibial tunnel 210, across the interior of knee joint 205, and up into the femoral tunnel 220. If desired, inserter 15 may be cannulated, so that the inserter and helicoil are advanced over a guidewire of the sort well known in the art. As the distal tip of the inserter is advanced, the tapered seat-forming thread 75 first finds its way into the space between the graft ligament 230 and the side wall of femoral bone tunnel 220. Then, as the inserter is turned, tapered seat-forming thread 75 forms a seat into the tissue in advance of helicoil 10, and helicoil 10 is advanced into the tissue so that the turns of helical body 20 seat themselves in the seat formed by seat-forming thread 75. As this occurs, the graft ligament is driven laterally, into engagement with the opposing side wall of the bone tunnel. This action sets helicoil 10 between the side wall of femoral bone tunnel 220 and graft ligament 230, thereby securing the interference fit between graft ligament 230 and the side wall of the bone tunnel, whereby to secure graft ligament 230 to the bone.

Figure 18:
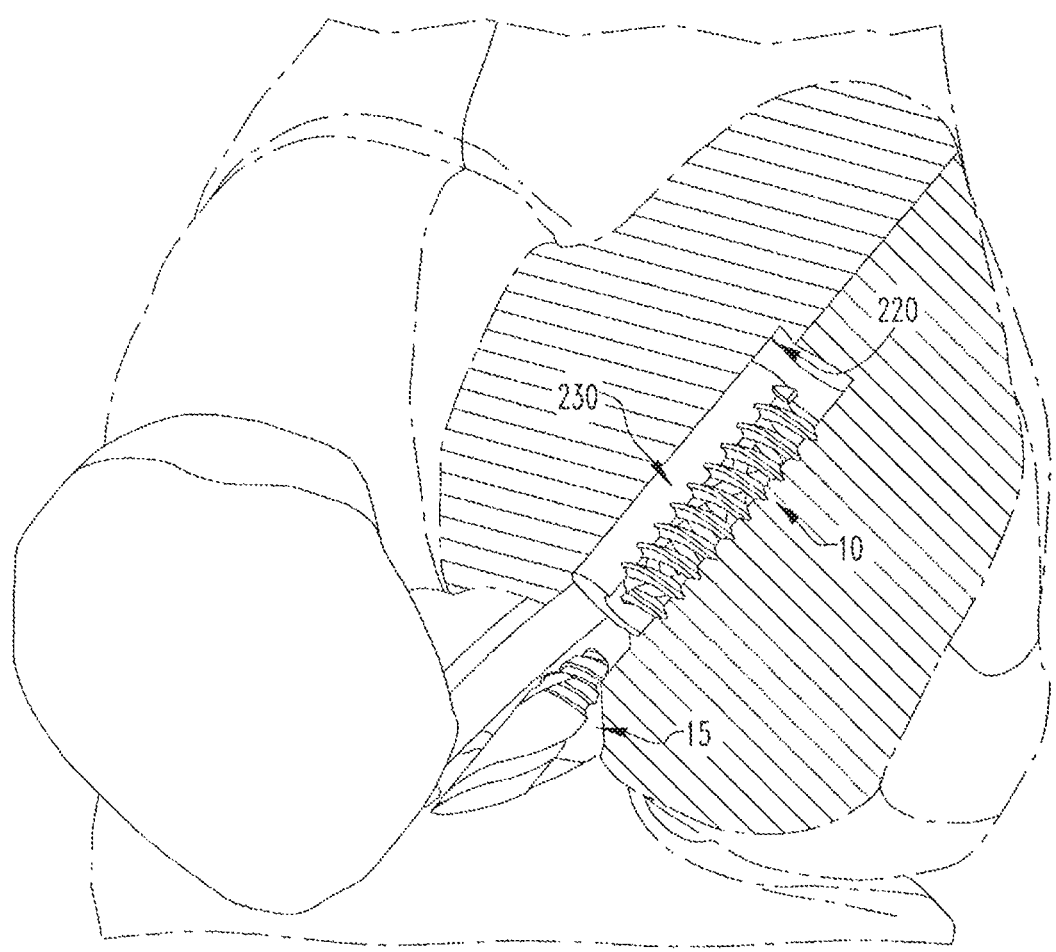
Figure 19:
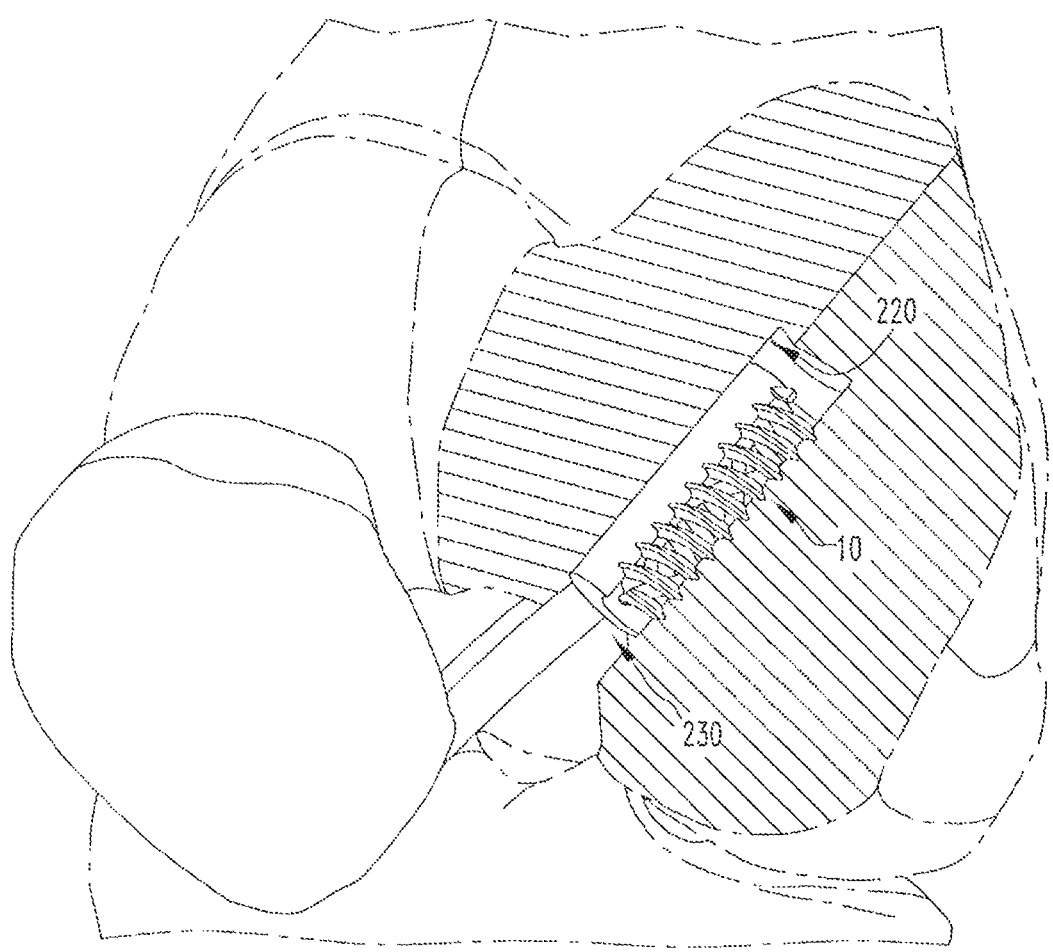
Figure 20:
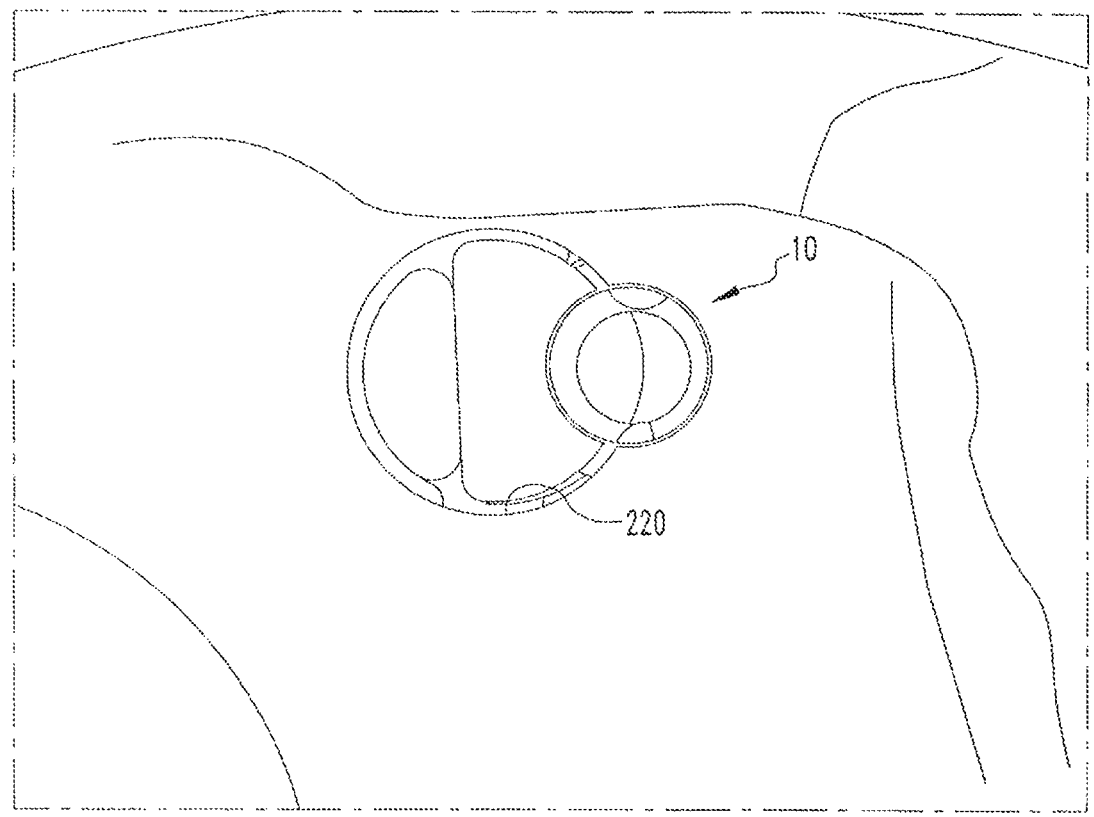
Figure 21:
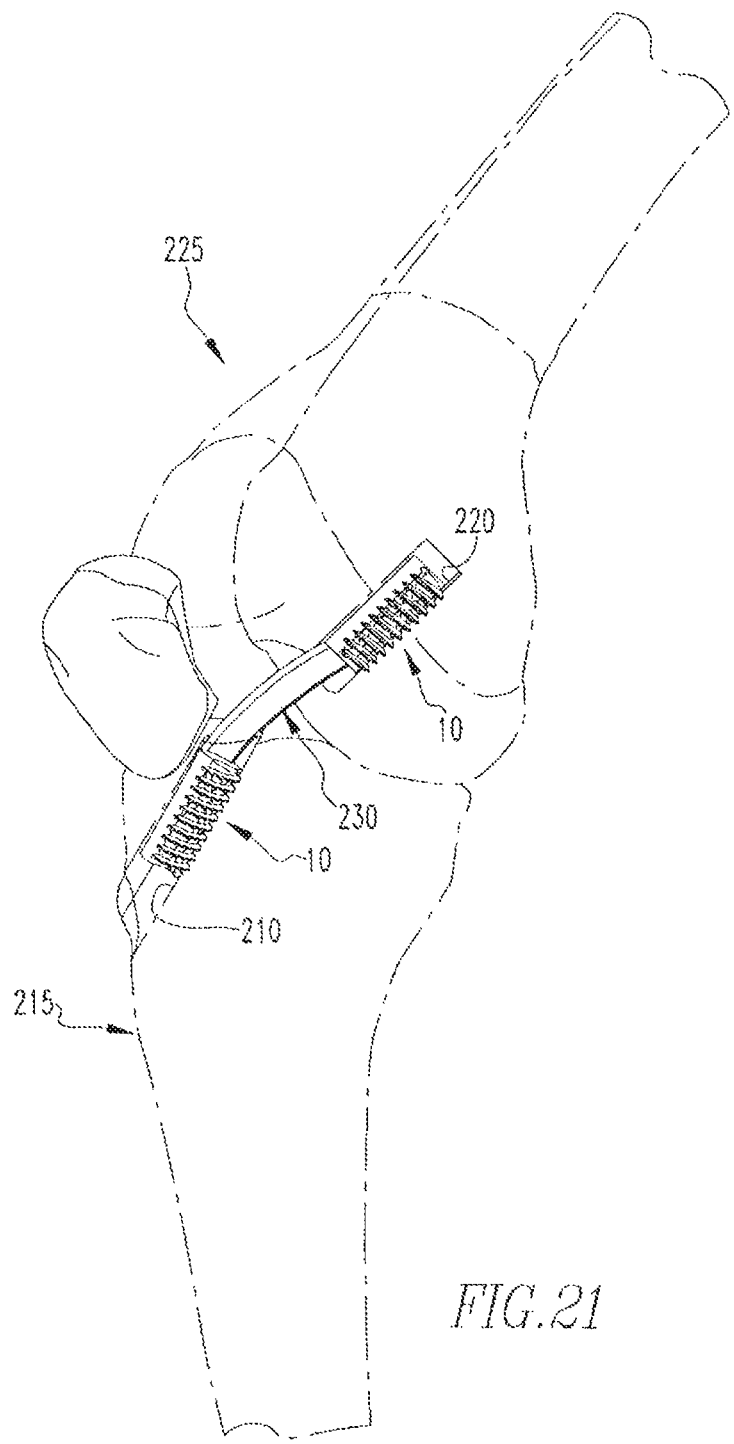
FIGS. 21-25 are schematic views showing a full ACL reconstruction using the second helicoil interference fixation system of FIGS. 8-13.
Figure 22:
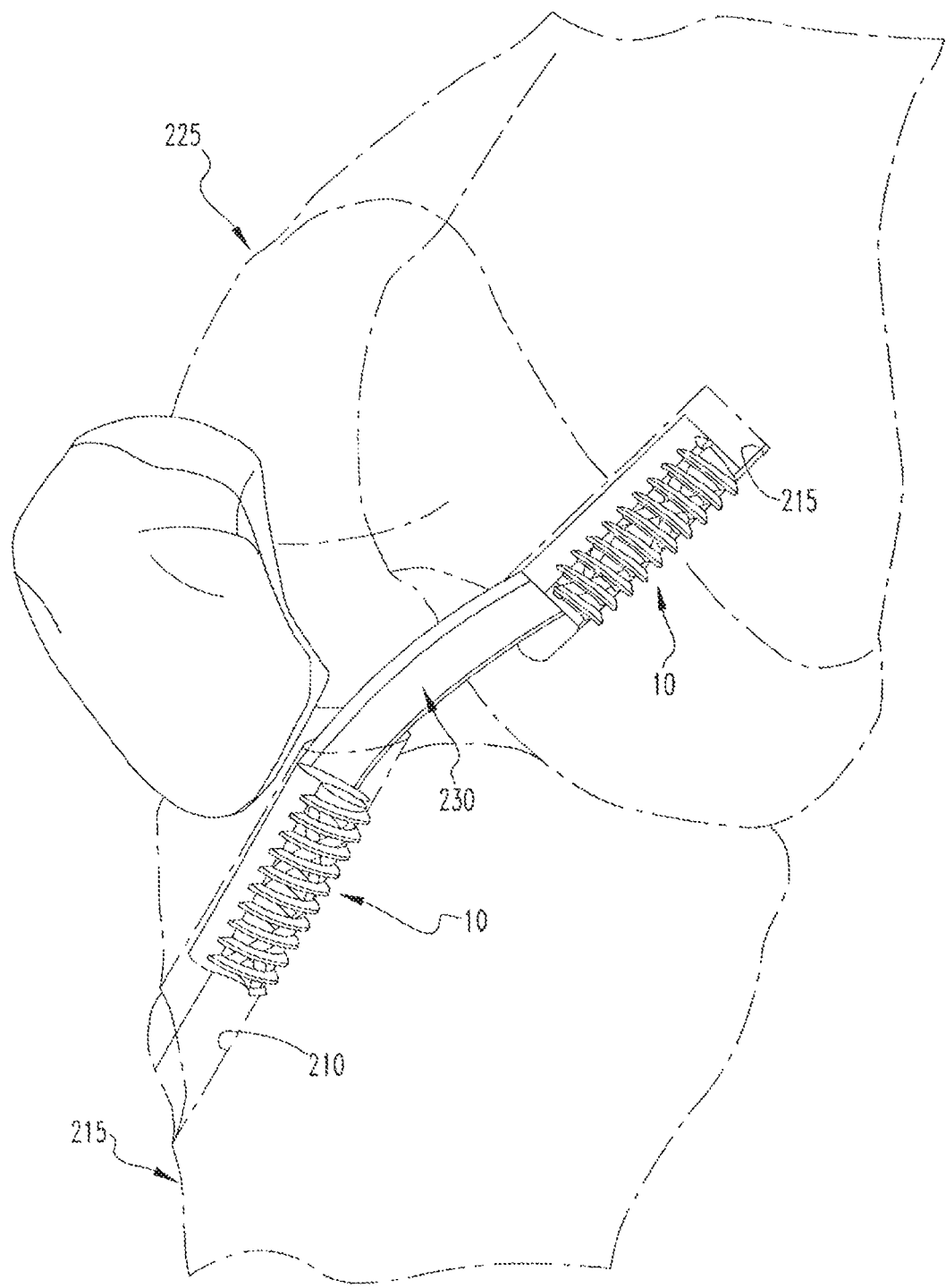
Figure 23:
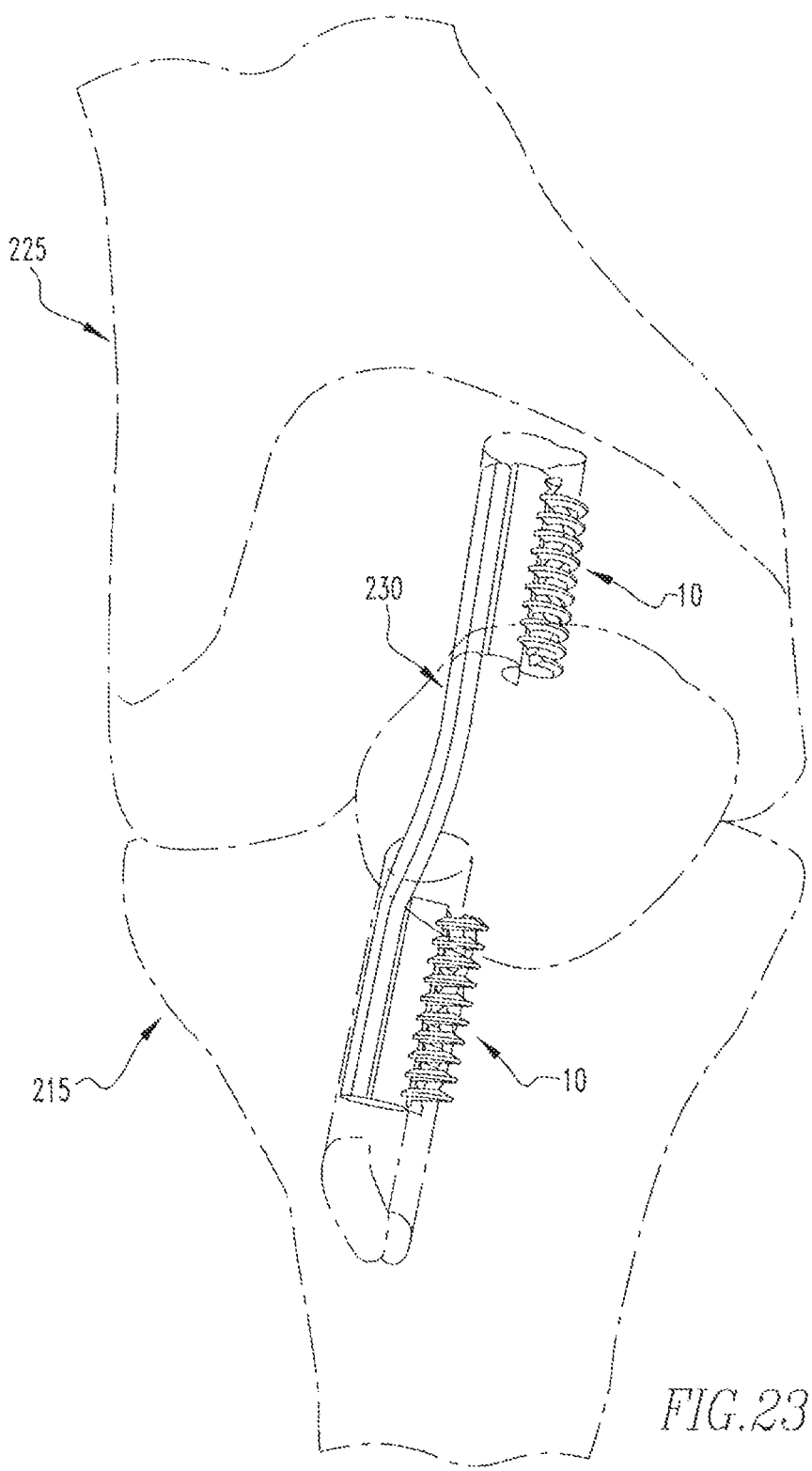
Figure 24:
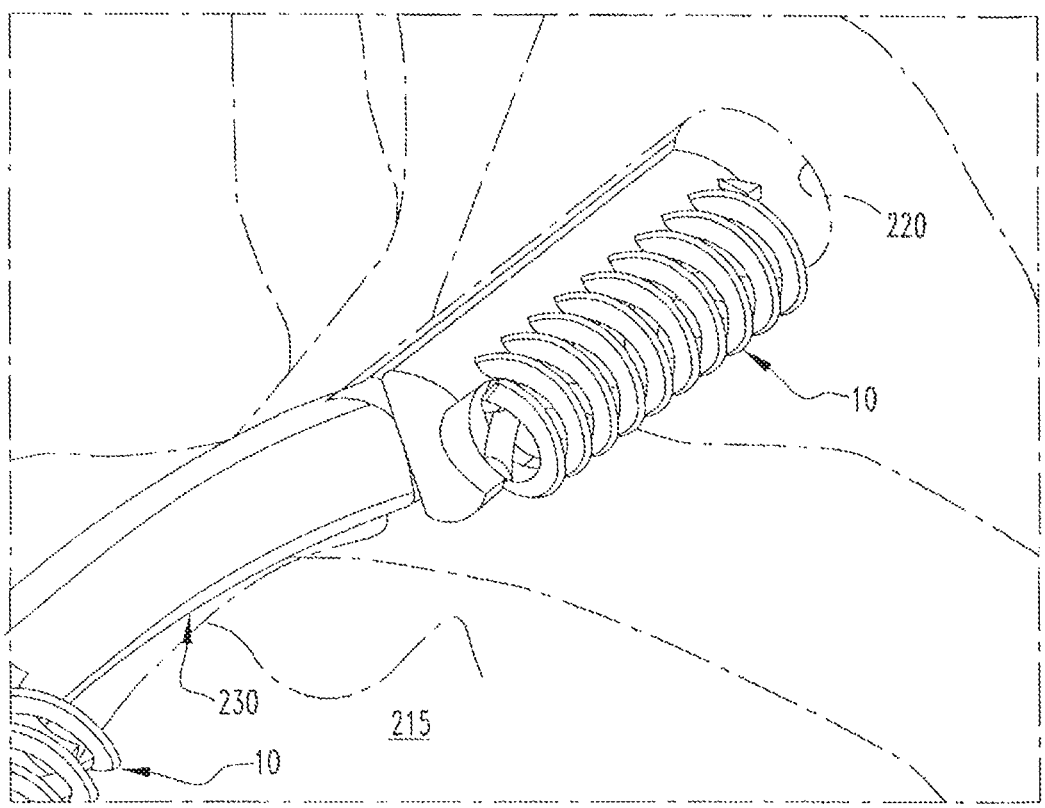
Figure 25:
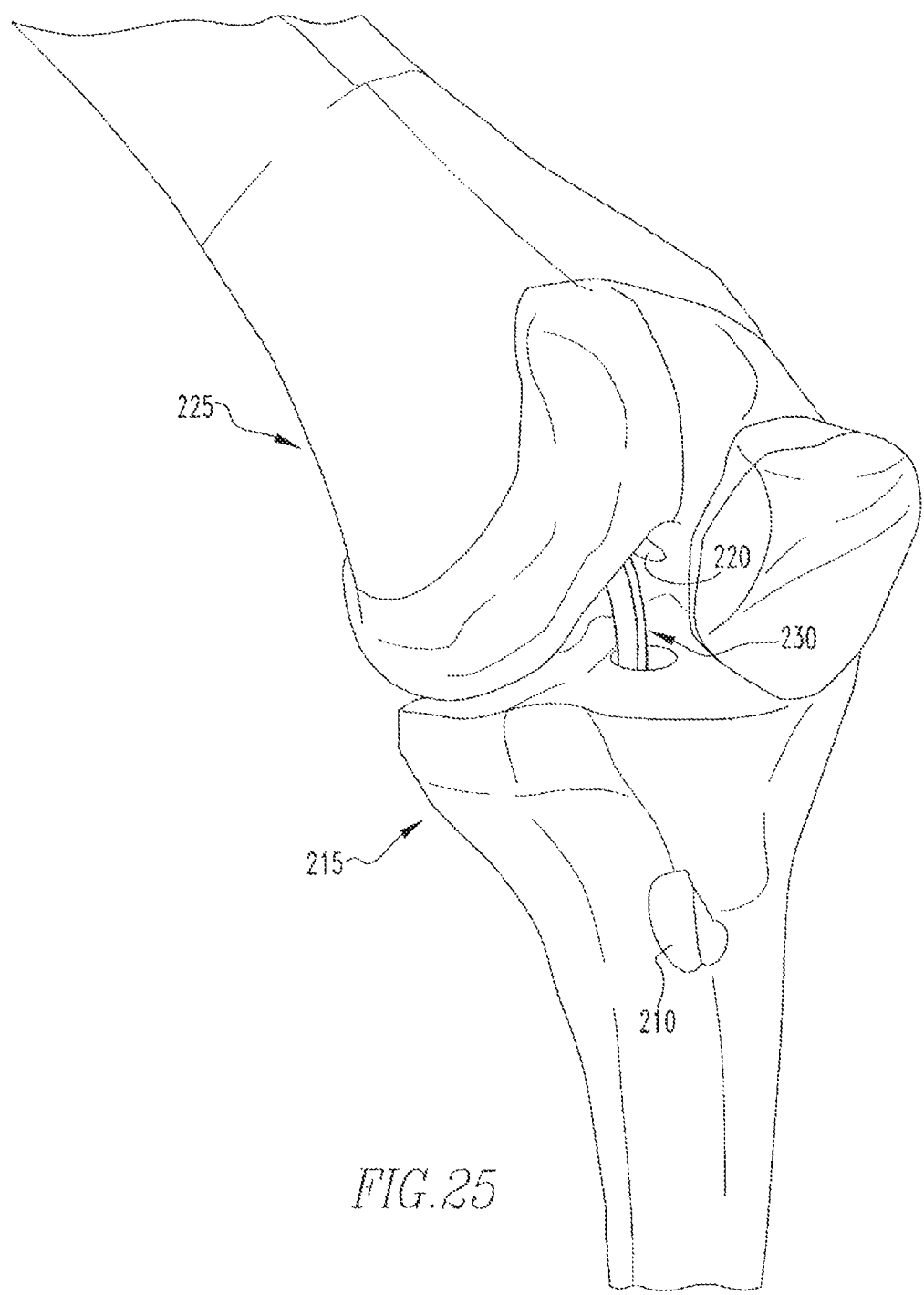

Thereafter, and looking now at FIGS. 18 and 19, inserter 15 is withdrawn, leaving helicoil 10 lodged in position between the graft ligament and the side wall of the bone tunnel. As seen in FIG. 20, helicoil 10 maintains the interference fit established between graft ligament 220 and the side wall of the bone tunnel, thereby securing the graft ligament to the bone.

If desired, helicoil interference fixation system 5 can then be used, in a similar manner to form a tibial fixation. See FIGS. 21-25.

Significantly, forming the fixation device in the form of an open helical coil has proven particularly advantageous, inasmuch as the open helical coil provides the strength needed to set the fixation device into position, and hold the graft ligament in position while bone-to-ligament in-growth occurs, while still providing extraordinary access through the body of the fixation device. Thus, cell- and nutrient-bearing fluids can move substantially unimpeded, through the body of helicoil 10, and tissue in-growth can occur across the body of helicoil 10.

Furthermore, it has been found that when the graft ligament thereafter imposes axial loads on the interference fit, struts 45 help maintain the structural integrity of turns 40 of helical body 20, whereby to ensure the integrity of the interference fit.

Figure 26:
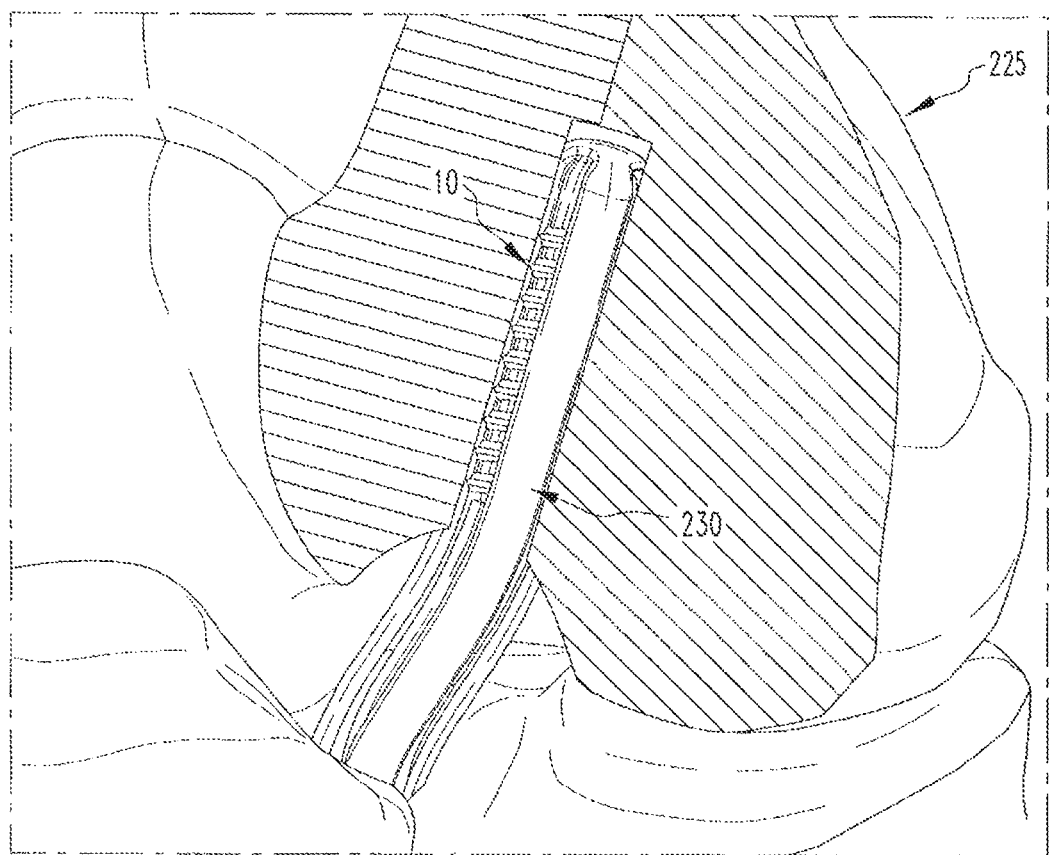
FIGS. 26-28 are schematic views showing a soft tissue ACL fixation using the second helicoil interference fixation system of FIGS. 8-13.
Figure 27:
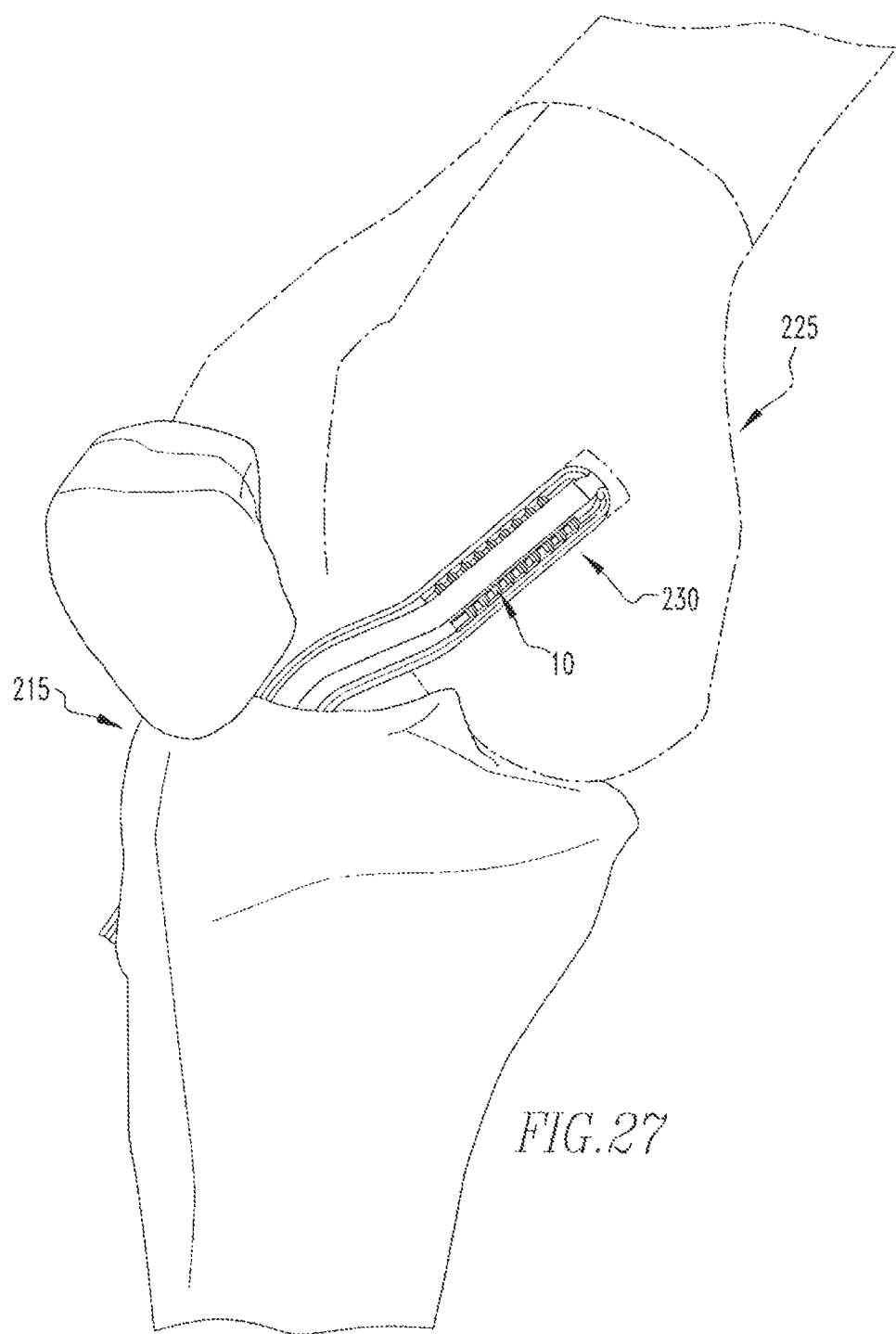
Figure 28:
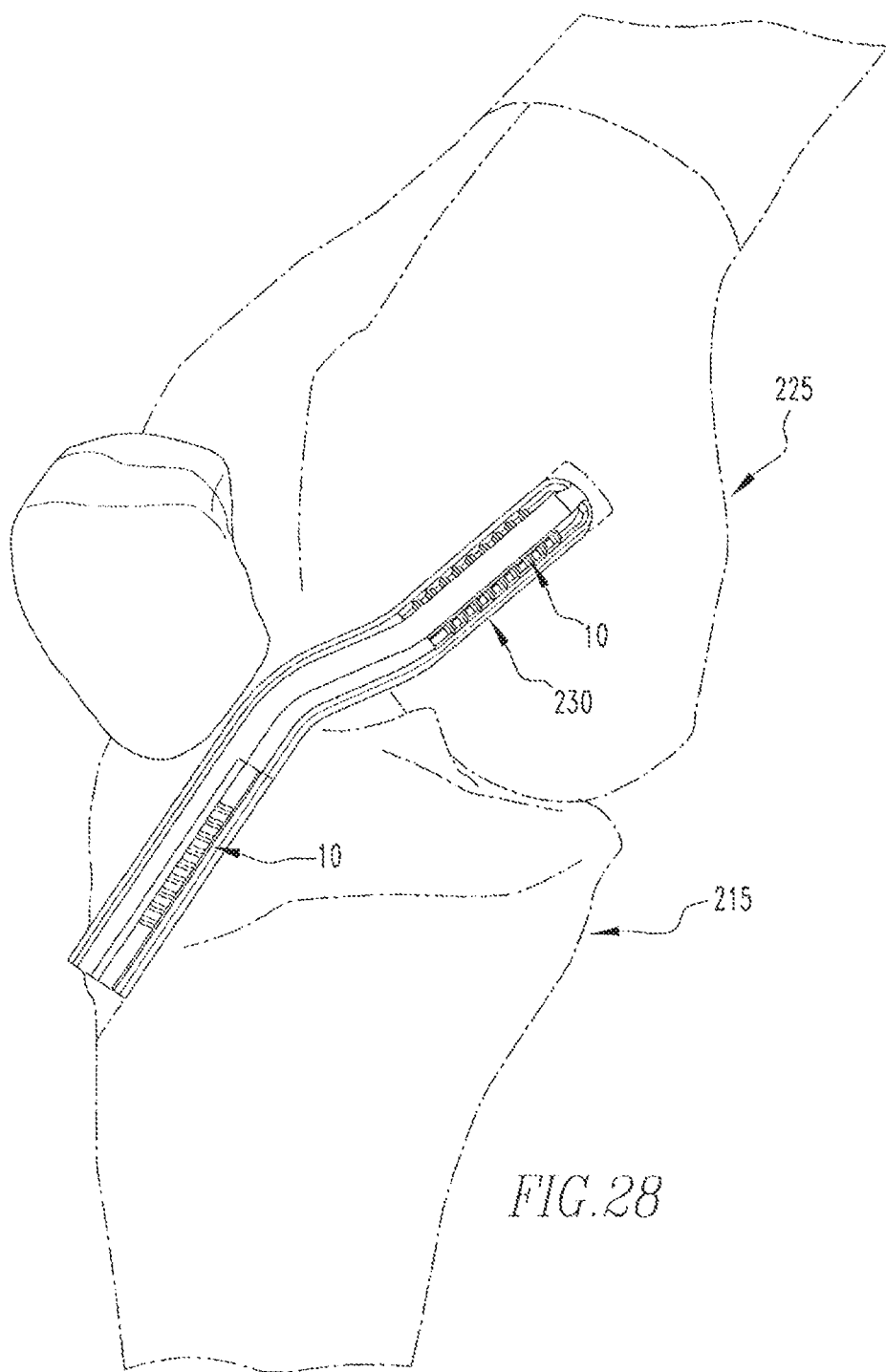

In FIGS. 16-24, graft ligament 230 is shown to include bone blocks at the ends of the ligament, e.g., graft ligament 10 may be a patella tendon with bone blocks attached. However, as seen in FIGS. 26-28, graft ligament 230 can also constitute only soft tissue, e.g., graft ligament 230 may comprise a semitendinosus tendon and/or a gracilis tendon, and/or a synthetic device.

Figure 11:
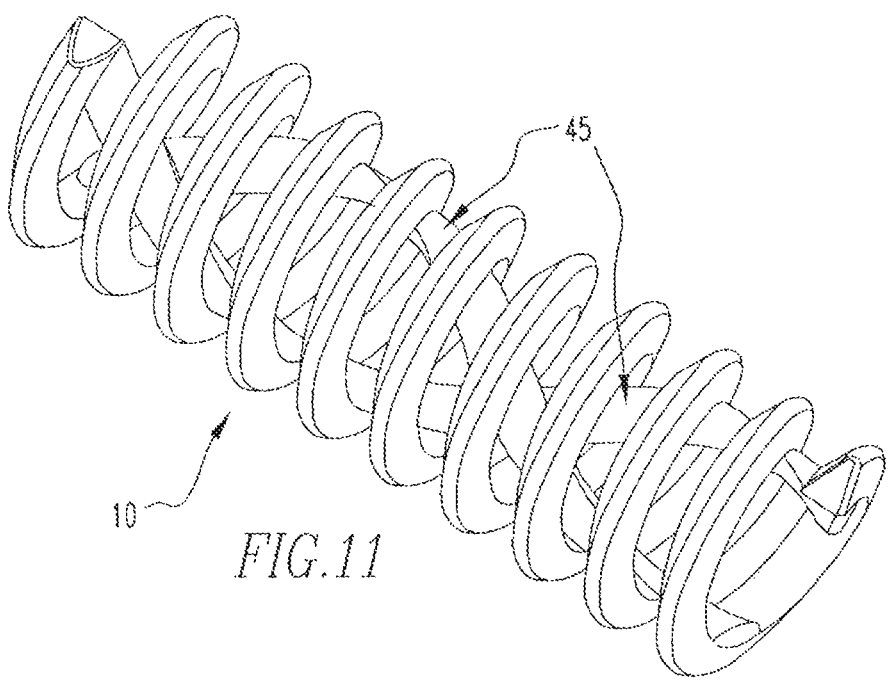
Figure 12:
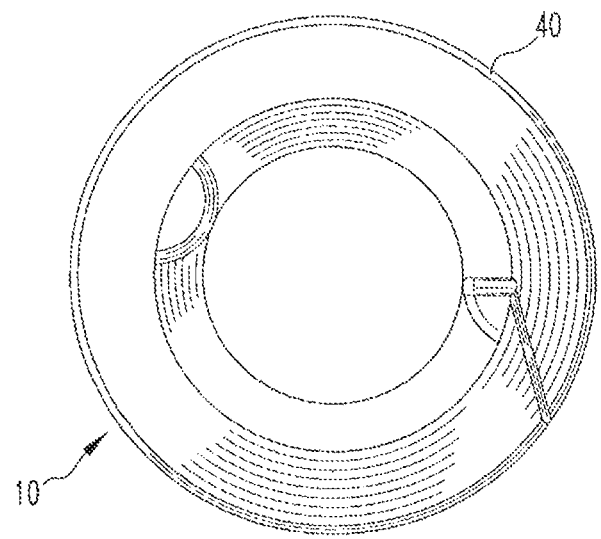
Figure 13:
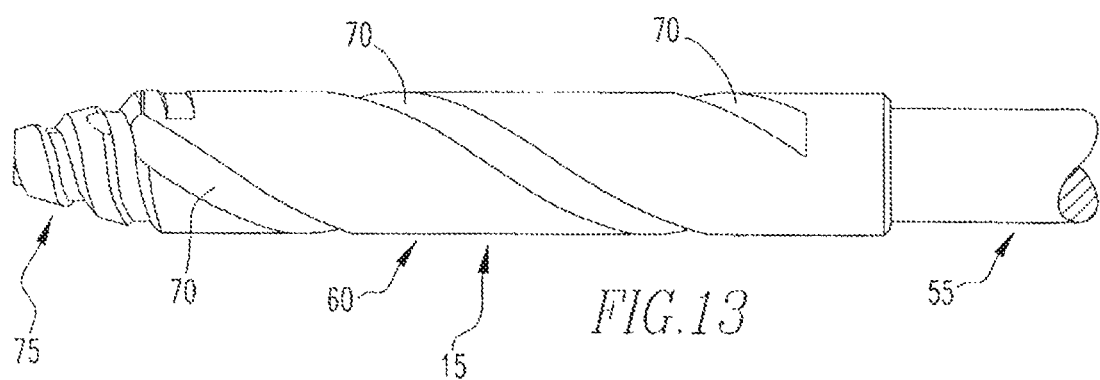
Figure 29:
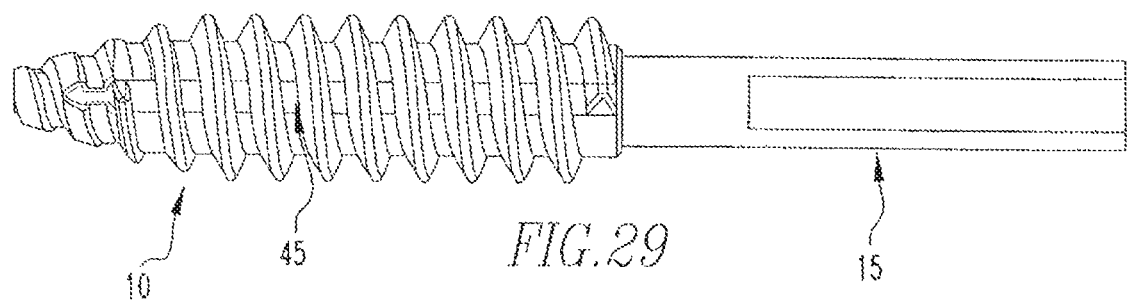
FIGS. 29-31 are schematic views showing a third helicoil interference fixation system formed in accordance with the present invention.
Figure 30:
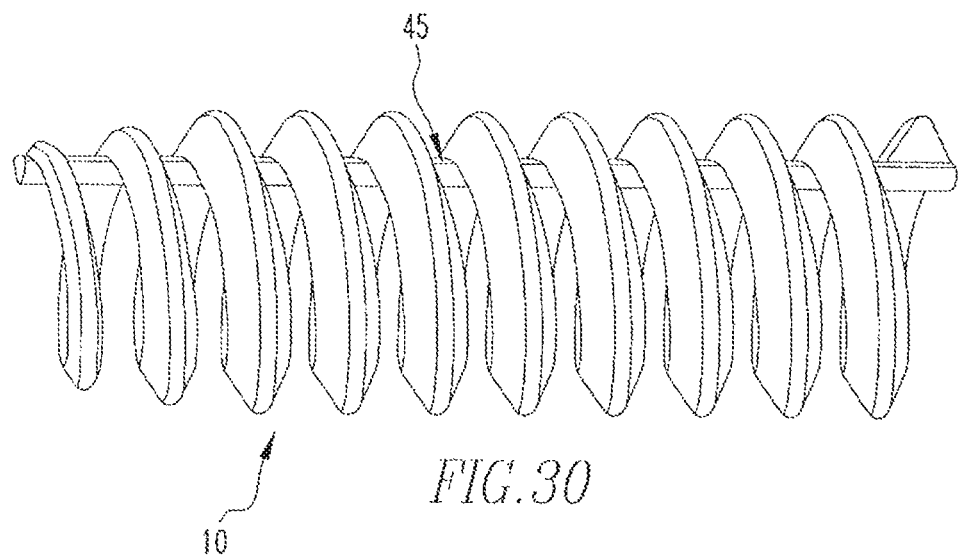
Figure 31:
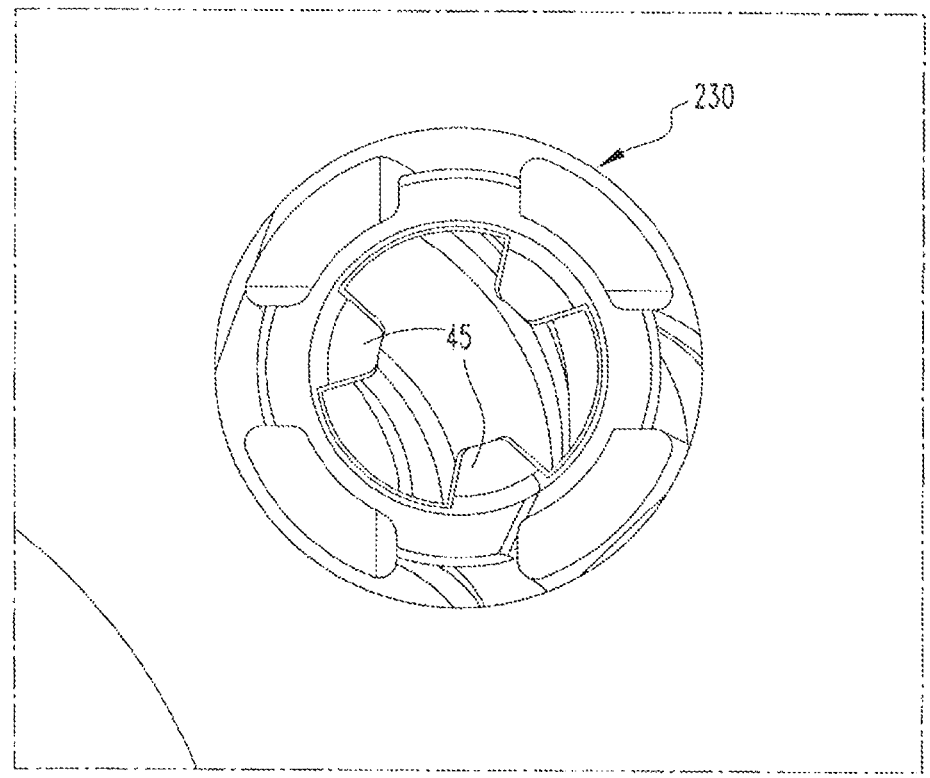

In FIGS. 5 and 11, the one or more struts 45 are shown as having a helical structure. However, the one or more struts 45 may also be formed with a straight configuration. See, for example, FIGS. 29-30, which show a helicoil 10 with a single straight strut 45, and FIG. 31 which shows a helicoil 10 with multiple straight struts 45.

Figure 32:
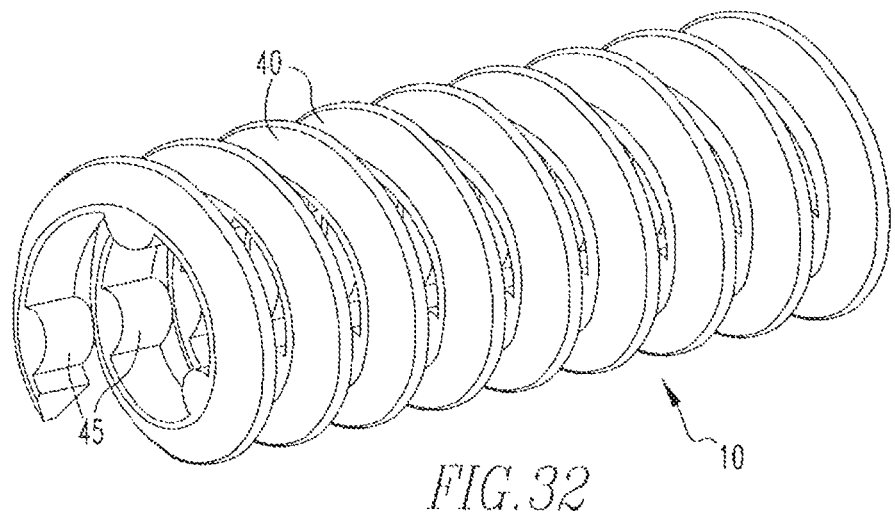
FIG. 32 is schematic view showing a fourth helicoil interference fixation system formed in accordance with the present invention.
Figure 33:
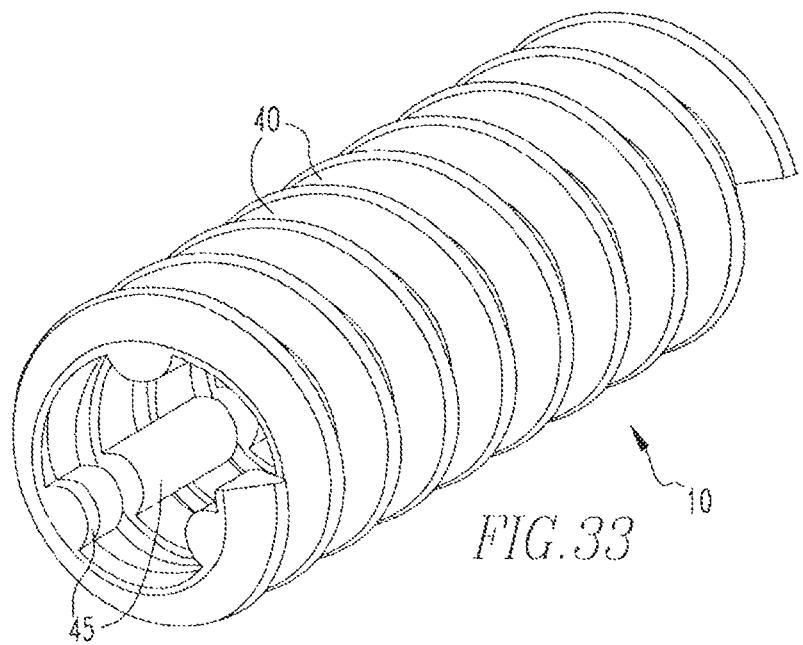
FIG. 33 is a schematic view showing a fifth helicoil interference fixation system formed in accordance with the present invention.

Furthermore, as seen in FIG. 32, the one or more struts 45 may be interrupted between turns 40 or, as seen in FIG. 33, the one or more struts 45 may be selectively interrupted between turns 40.

Figure 34:
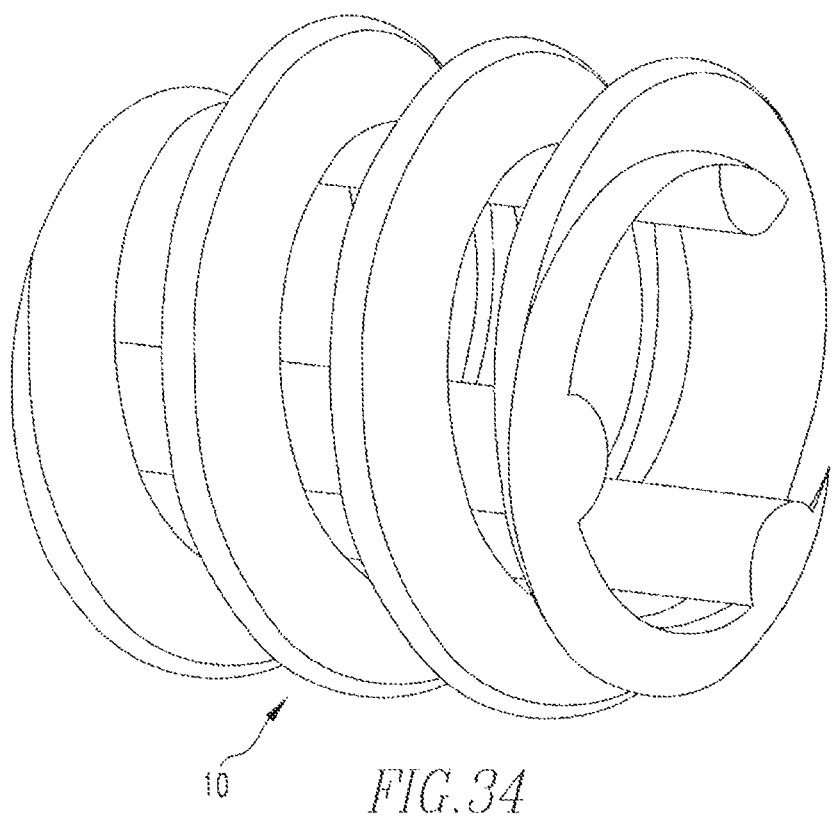
FIGS. 34-36 are schematic views showing a sixth helicoil interference fixation system formed in accordance with the present invention.
Figure 35:
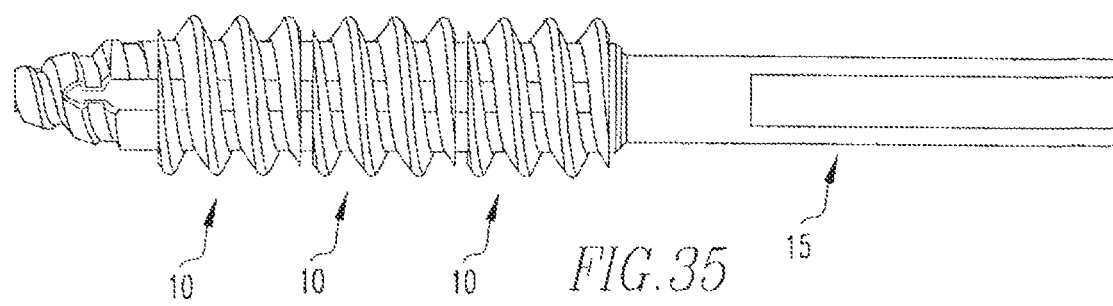
Figure 36:
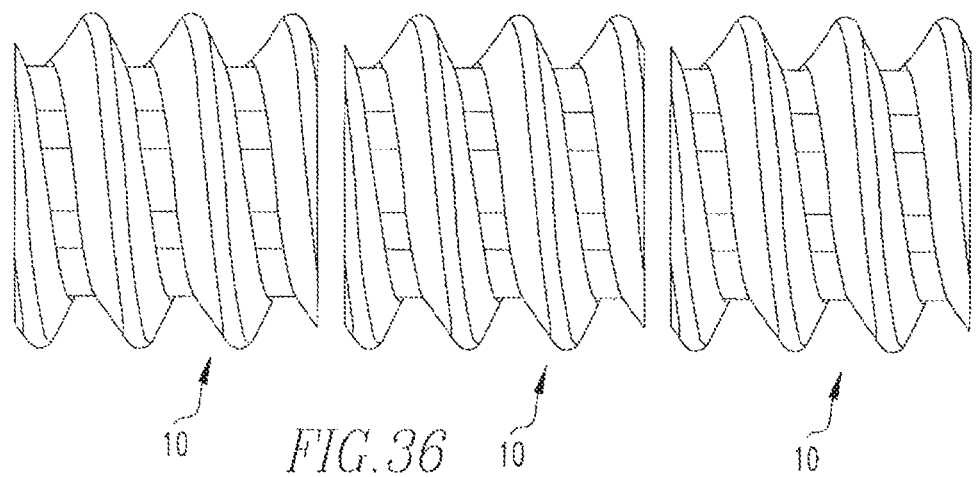

It should also be appreciated that an interference fit may be formed using a plurality of helicoils 10. Thus, as seen in FIGS. 34-36, a plurality of helicoils 10 may be loaded on an inserter 15 and used for a collective interference fit.

Figure 37:
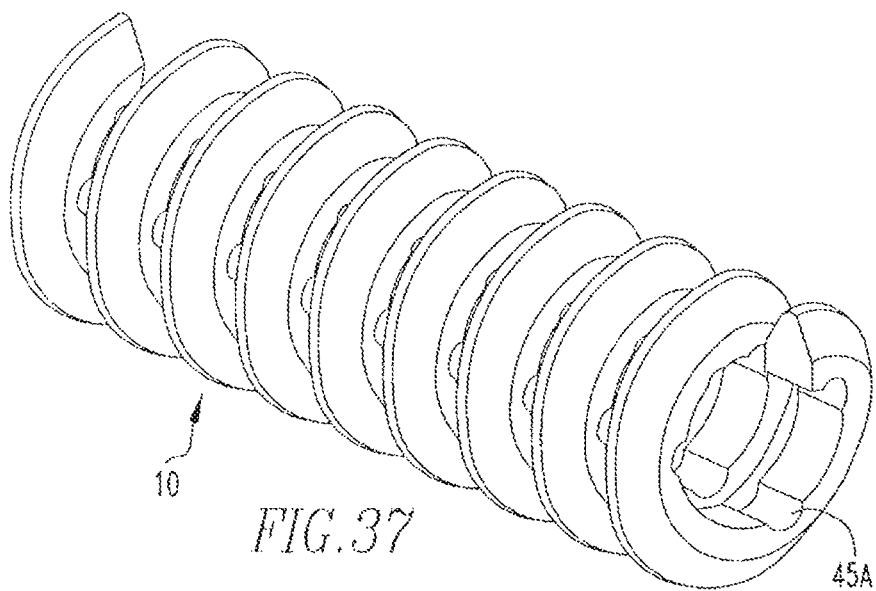
FIG. 37 is a schematic view showing a seventh helicoil interference fixation system formed in accordance with the present invention.

If desired, and looking now at FIG. 37, the one or more struts 45 may be replaced with recesses 45A. In this case, grooves 70 on inserter 15 are replaced by corresponding ribs (not shown), whereby to permit inserter 15 to rotatably drive helicoil 10.

Figure 38:
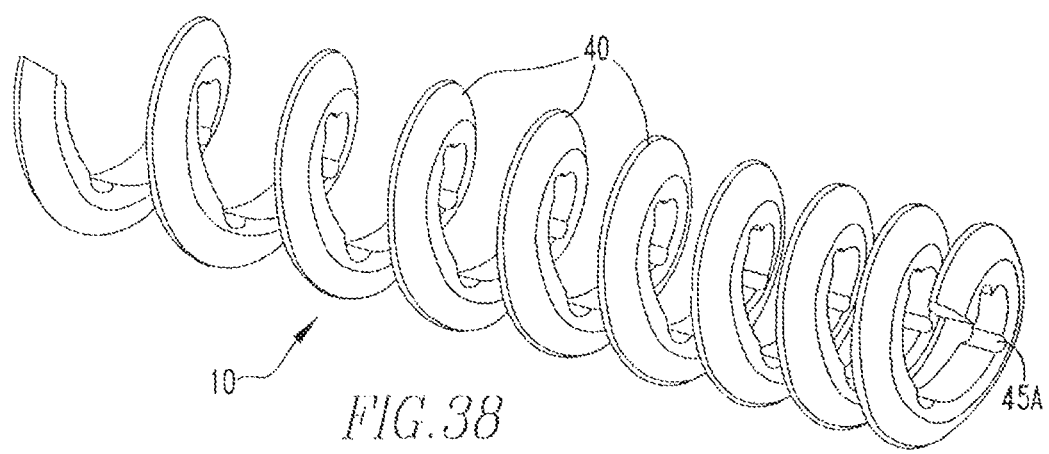
FIG. 38 is a schematic view showing an eighth helicoil interference fixation system formed in accordance with the present invention.
Figure 39:
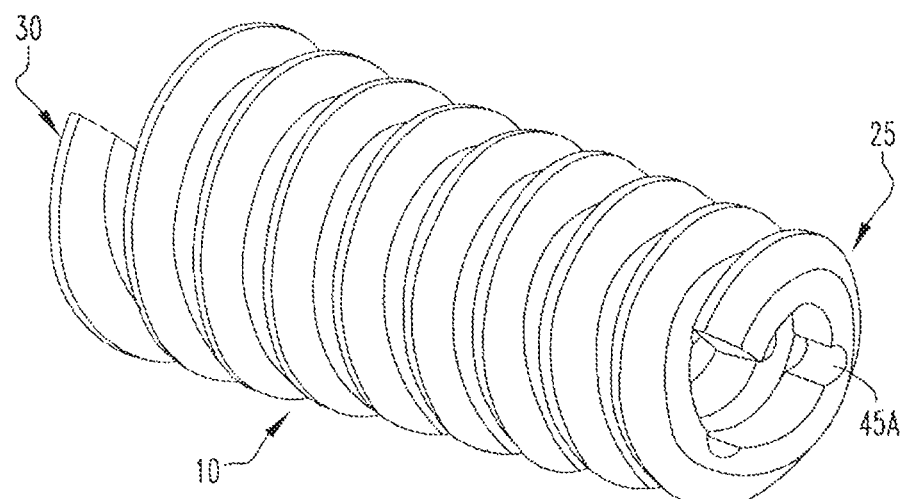
FIG. 39 is a schematic view showing a ninth helicoil interference fixation system formed in accordance with the present invention.

As seen in FIG. 38, the period of turns 40 may change along the length of helicoil 10.

Additionally, if desired, helicoil 10 can be tapered between its distal end 25 and its proximal end 30.

MODIFICATIONS

It will be appreciated that still further embodiments of the present invention will be apparent to those skilled in the art in view of the present disclosure. It is to be understood that the present invention is by no means limited to the particular constructions and method steps herein disclosed and/or shown in the drawings, but also comprises any modifications or equivalents within the scope of the invention.

What is claimed is:

1. An anchor assembly comprising:
a driver comprising:
a cannulated shaft including a proximal end, a distal end, and a longitudinal axis extending therebetween, the distal end of the shaft comprising a first drive surface; and
a handle coupled to the shaft and aligned with the longitudinal axis, a diameter of the handle larger than a diameter of the shaft; and
an anchor engageable with the driver, the anchor comprising:
a cannulated body including a helical thread extending between a distal end and a proximal end of the body, the body having at least one opening between turns of the thread;
a second drive surface at least partially defined by an interior surface of the body, the second drive surface extending a fixed length from the proximal end to the distal end of the body and contacting at least two turns of the turns of the thread;
wherein the distal end of the shaft of the driver receives an entire length of the second drive surface of the anchor when the anchor is engaged with the driver such that a portion of the first drive surface is distal to the anchor.

2. The anchor assembly of claim 1, wherein the second drive surface closes off less than fifty percent of each opening of the at least one opening between adjacent turns of the thread along which the drive surface extends.

3. The anchor assembly of claim 1, wherein the first drive surface comprises at least one groove and the second drive surface comprises at least one runner.

4. The anchor assembly of claim 1, wherein the distal end of the shaft of the driver supports the entire length of the second drive surface of the anchor when the anchor is inserted into bone.

5. The anchor assembly of claim 1, wherein the anchor comprises an absorbable material.

6. The anchor assembly of claim 1, wherein the anchor comprises a non-absorbable material.

7. An anchor assembly comprising:
a driver comprising:
a cannulated shaft including a proximal end, a distal end, and a longitudinal axis extending therebetween, the distal end of the shaft comprising a first drive surface; and
a handle coupled to the shaft and aligned with the longitudinal axis, a diameter of the handle larger than a diameter of the shaft; and
an anchor engageable with the driver, the anchor comprising:
a cannulated body including a helical thread extending between a distal end and a proximal end of the body, the body having at least one opening between turns of the thread; and
a second drive surface at least partially defined by an interior surface of the body, the second drive surface extending a fixed length from the proximal end to the distal end of the body and contacting at least two turns of the turns of the thread, the distal end of the shaft of the driver receiving an entire length of the second drive surface of the anchor when the anchor is engaged with the driver such that a portion of the first drive surface is distal to the anchor;
wherein a distal end of the anchor assembly comprises a tapered tip.

8. The anchor assembly of claim 7, wherein the second drive surface closes off less than fifty percent of each opening of the at least one opening between adjacent turns of the thread along which the drive surface extends.

9. The anchor assembly of claim 7, wherein the first drive surface comprises at least one groove and the second drive surface comprises at least one runner.

10. The anchor assembly of claim 7, wherein the distal end of the shaft of the driver supports the entire length of the second drive surface of the anchor when the anchor is inserted into bone.

11. The anchor assembly of claim 7, wherein the anchor comprises an absorbable material.

12. The anchor assembly of claim 7, wherein the anchor comprises a non-absorbable material.

13. The anchor assembly of claim 7, wherein the tapered tip is configured to facilitate insertion of the anchor into bone.

14. An anchor assembly comprising:
a driver comprising:
a cannulated shaft including a proximal end, a distal end, and a longitudinal axis extending therebetween, the distal end of the driver including a first drive surface and a tip; and
a handle coupled to the shaft and aligned with the longitudinal axis, a diameter of the handle larger than a diameter of the shaft; and
an anchor engageable with the driver, the anchor comprising:
a cannulated body including a helical thread extending between a distal end and a proximal end of the body, the body defining at least one opening between turns of the thread;
a second drive surface at least partially defined by an interior surface of the body, the second drive surface extending a fixed length from the proximal end to the distal end of the body and contacting at least two turns of the turns of the thread;
wherein the distal end of the shaft of the driver receives an entire length of the second drive surface of the anchor when the anchor is engaged with the driver, such that a portion of the first drive surface is distal to the anchor; and
wherein, when the anchor is engaged with the driver, the tip is located distal to the anchor.

15. The anchor assembly of claim 14 wherein the second drive surface closes off less than fifty percent of each opening of the at least one opening between adjacent turns of the thread along which the drive surface extends.

16. The anchor assembly of claim 14, wherein the first drive surface comprises at least one groove and the second drive surface comprises at least one runner.

17. The anchor assembly of claim 14, wherein the distal end of the shaft of the driver supports the entire length of the second drive surface of the anchor when the anchor is inserted into bone.

18. The anchor assembly of claim 14, wherein the anchor comprises an absorbable material.

19. The anchor assembly of claim 14, wherein the anchor comprises a non-absorbable material.

20. The anchor assembly of claim 14, wherein the tip is configured to facilitate insertion of the anchor into bone.

* * * * *